US006908735B2

(12) United States Patent
Nunomura

(10) Patent No.: US 6,908,735 B2
(45) Date of Patent: Jun. 21, 2005

(54) POLYNUCLEOTIDE QUANTITATION METHOD

(75) Inventor: Kiyotada Nunomura, Tanashi (JP)

(73) Assignee: Gen-Probe Incorporated, San Diego, CA (US)

( * ) Notice: Subject to any disclaimer, the term of this patent is extended or adjusted under 35 U.S.C. 154(b) by 0 days.

(21) Appl. No.: 09/943,286

(22) Filed: Aug. 30, 2001

(65) Prior Publication Data

US 2002/0106668 A1 Aug. 8, 2002

Related U.S. Application Data

(63) Continuation of application No. 09/620,958, filed on Jul. 21, 2000, now Pat. No. 6,294,338.
(60) Provisional application No. 60/145,432, filed on Jul. 23, 1999.

(51) Int. Cl.[7] .......................... C12Q 1/68; C12P 19/34; C07H 21/02; C07H 21/04

(52) U.S. Cl. ......................... 435/6; 435/91.2; 536/23.1; 536/24.3

(58) Field of Search .......................... 435/6, 91.2, 91.1; 536/23.1, 24.3

(56) References Cited

U.S. PATENT DOCUMENTS

| | | | | |
|---|---|---|---|---|
| 4,683,195 A | | 7/1987 | Mullis et al. | 435/6 |
| 5,219,727 A | | 6/1993 | Wang et al. | 435/6 |
| 5,283,174 A | | 2/1994 | Arnold, Jr. et al. | 435/6 |
| 5,399,491 A | | 3/1995 | Kacian et al. | 435/91.21 |
| 5,705,365 A | | 1/1998 | Ryder et al. | 435/91.1 |
| 5,710,029 A | | 1/1998 | Ryder et al. | 435/91.1 |
| 5,952,202 A | * | 9/1999 | Aoyagi et al. | 435/91.2 |

FOREIGN PATENT DOCUMENTS

| | | |
|---|---|---|
| EP | 0320308 | 6/1989 |
| EP | 0497272 | 8/1992 |
| EP | 0525882 | 2/1993 |
| EP | 0587266 | 3/1994 |
| EP | 0587298 | 3/1994 |
| EP | 0623682 | 11/1994 |
| EP | 0731174 A2 | 9/1996 |
| WO | 9102818 | 3/1991 |
| WO | 9302215 | 2/1993 |
| WO | WO 9502067 A1 | 1/1995 |
| WO | 9503430 | 2/1995 |
| WO | WO 9858086 A2 | 12/1998 |

OTHER PUBLICATIONS van Gemen, B. et al., "A one–tube quantitative HIV–1 RNA NASBA nucleic acid amplification assay using electrochemiluminescent (ECL) labelled probes", J. Virol. Methods, vol. 49, pp. 157–168 (1994).*

Jurriaans, S. et al., "Fluctuations is steady state level of genomic HIV–1 RNA and replication intermediates related to disease progression rate", Immunol. Letters, vol. 51, pp. 15–22 (1996).*

Rosenstraus, M. et al., "An Internal Control for Routine Diagnostic PCR: Design, Properties, and Effect on Clinical Performance", J. Clin. Microbiol., vol. 36, pp. 191–198 (Jan. 1998).*

Kricka, L.J., "Chemiluminescent and Bioluminescent Teachniques", Clin. Chem., vol. 37, pp. 1472–1481 (1991).*

Chelly et al., :Transcription of the dystrophin gene in human muscle and non–muscle tissues, *Nature*, 333:858–860 (Jun. 1988).

Porsing, "In Vitro Nucleic Acid Amplification Techniques", *Diagnostic Molecular Microbiology—Principles and Applications*, (Persing et al. , eds.) Part I, Chpt. 3, *citing 2 sections*: Quantitative PCR and Transcription–Based Amplification Systems: TAS and 3SR (incl. Figure 4,), pp. 65–67 (1993)*.

van Gemen et al., "A one–tube quantitative HIV–1 RNA NASBA nucleic acid amplification assay using electrochemiluminescent (ECL) labelled probes", *J. Virol. Meth.*, 49:157–168 (1994)*.

Natarajan V. et al., "An Internally Controlled Virion PCR for the Measurement of HIV–1 RNA in Plasma", PCR Methods and Applications, vol. 3, pp. 346–350 (Jun. 1994).

Ratner et al., "Complete Nucleotide Sequence of the AIDS Virus, HTLV–III", Nature, Jan. 1985, 313:277–284.

Van Beveran et al., "Appendix B: HTLV–3 genone", RNA Tumor Viruses, Molecular Biology of Tumor Viruses, Second Edition, 1985, 2:1106–1123.

Hostomsky et al., "Reconstitution in vitro of RNase H Activity by Using Purified N–terminal and C–terminal Domains of Human Immunodeficiency Virus Type 1 Reverse Transcriptase", Proc. Natl. Acad. Sci. USA, Feb. 1991, 88:1148–1152.

Erlich et al., "The Design and Optimization of the PCR", PCR Technology, 1989, Chp. 1, pp. 14–15, Stockton Press, US, XP002183252.

(Continued)

*Primary Examiner*—Jeffrey Fredman
*Assistant Examiner*—Teresa Strzelecka
(74) *Attorney, Agent, or Firm*—Michael J. Gilly

(57) ABSTRACT

Methods useful for improving results obtained with enzyme-based polynucleotide amplification reactions. More particularly, the invented methods are useful for: (1) promoting amplification of template-specific products such that the amount of amplicon produced reflects the pre-amplification amount of analyte, even in reactions primed with low levels of analyte polynucleotide; (2) facilitating biological specimen processing such that the amount of amplicon produced in subsequent amplification reactions will be substantially independent of the efficiency of analyte polynucleotide isolation from the specimen; and (3) controlling the amount of analyte amplicon produced in the amplification reaction.

6 Claims, 7 Drawing Sheets

OTHER PUBLICATIONS

Innis et al., "PCR Protocals—A Guide to Method and Applications", 1989, pp. 10, Academic Press, San Diego, US, XP002183253.
Kellogg et al., "Quantitation of HIV–1 Proviral DNA Relative to Cellular DNA by the Polymerase Chain Reaction", Anal. Biochem., Sep. 1990, 189(2):202–208.
Piatak et al., "Quantitative Competitive Polymerase Chain Reaction for Accurate Quantitation of HIV DNA and RNA Species", BioTechniques, Jan. 1993, 14(1):70–81.
Van Gemen et al., "The One–tube Quantitative HIV–1 RNA NASBA: Precision, Accuracy, and Application", PCR Methods Appl. Feb. 1995, 4(4):S177–S184.

* cited by examiner

SEQUENCE LISTING

<160> NUMBER OF SEQ ID NOS: 9

<210> SEQ ID NO 1
<211> LENGTH: 55
<212> TYPE: DNA
<213> ORGANISM: Artificial Sequence
<220> FEATURE:
<223> OTHER INFORMATION: Primer T7A(-)4190

<400> SEQUENCE: 1
aatttaatac gactcactat agggagagtt tgtatgtctg ttgctattat gtcta 55

<210> SEQ ID NO 2
<211> LENGTH: 19
<212> TYPE: DNA
<213> ORGANISM: Artificial Sequence
<220> FEATURE:
<223> OTHER INFORMATION: Primer (+)4108

<400> SEQUENCE: 2
acagcagtac aaatggcag 19

<210> SEQ ID NO 3
<211> LENGTH: 8933
<212> TYPE: RNA
<213> ORGANISM: Human Immunodeficiency Virus
<220> FEATURE:
<221> NAME/KEY: source
<222> LOCATION: (1)...(8933)
<223> OTHER INFORMATION: Sequence of transcripts produced from the BH10
plasmid.

<400> SEQUENCE: 3
gagcucucuc gacgcaggac ucggcuugcu gaagcgcgca cggcaagagg cgaggggcgg 60
cgacugguga guacgccaaa aauuuugacu agcggaggcu agaaggagag agaugggugc 120
gagagcguca guauuaagcg ggggagaauu agaucgaugg gaaaaaauuc gguuaaggcc 180
agggggaaag aaaaaauaua aauuaaaaca uauaguaugg gcaagcaggg agcuagaacg 240
auucgcaguu aauccuggcc uguuagaaac aucagaaggc uguagacaaa uacugggaca 300
gcuacaacca ucccuucaga caggaucaga agaacuuaga ucauuauaua auacaguagc 360
aacccucuau ugugugcauc aaaggauaga gauaaaagac accaaggaag cuuuagacaa 420
gauagaggaa gagcaaaaca aaaguaagaa aaaagcacag caagcagcag cugacacagg 480
acacagcagu caggucagcc aaaauuaccc uauagugcag aacauccagg ggcaaauggu 540
acaucaggcc auaucaccua gaacuuuaaa ugcaugggua aaaguaguag aagagaaggc 600
uuucagccca gaaguaauac ccauguuuuc agcauuauca gaaggagcca ccccacaaga 660
uuuaaacacc augcuaaaca cagugggggg acaucaagca gccaugcaaa uguuaaaaga 720
gaccaucaau gaggaagcug cagaauggga uagaguacau ccagugcaug cagggccuau 780
ugcaccaggc cagaugagag aaccaagggg aagugacaua gcaggaacua cuaguacccu 840
ucaggaacaa auaggaugga ugacaaauaa uccaccuauc ccaguaggag aaauuuauaa 900
aagauggaua auccugggau uaaauaaaau aguaagaaug uauagcccua ccagcauucu 960
ggacauaaga caaggaccaa aagaaccuuu uagagacuau guagaccggu ucuauaaaac 1020
ucuaagagcc gagcaagcuu cacaggaggu aaaaaauugg augacagaaa ccuuguuggu 1080
ccaaaaugcg aacccagauu guaagacuau uuuaaaagca uugggaccag cggcuacacu 1140

-continued

```
agaagaaaug augacagcau gucagggagu aggaggaccc ggccauaagg caagaguuuu   1200
ggcugaagca augagccaag uaacaaauac agcuaccaua augaugcaga gaggcaauuu   1260
uaggaaccaa agaaagaugg uuaaguguuu caauuguggc aaagaagggc acacagccag   1320
aaauugcagg gccccuagga aaaagggcug uuggaaaugu ggaaaggaag gacaccaaau   1380
gaaagauugu acugagagac aggcuaauuu uuuagggaag aucuggccuu ccuacaaggg   1440
aaggccaggg aauuuucuuc agagcagacc agagccaaca gccccaccau uucuucagag   1500
cagaccagag ccaacagccc caccagaaga gagcuucagg ucuggggguag agacaacaac   1560
ucccccucag aagcaggagc cgauagacaa ggaacuguau ccuuuaacuu cccucagauc   1620
acucuuuggc aacgaccccu cgucacaaua aagauagggg ggcaacuaaa ggaagcucua   1680
uuagauacag gagcagauga uacaguauua gaagaaauga guuugccagg aagauggaaa   1740
ccaaaaauga uaggggggaau uggagguuuu aucaaaguaa gacaguauga ucagauacuc   1800
auagaaaucu guggacauaa agcuauaggu acaguauuag uaggaccuac accugucaac   1860
auaauuggaa gaaaucuguu gacucagauu gguugcacuu uaaauuuucc cauuagcccu   1920
auugagacug uaccaguaaa auuaaagcca ggaauggaug gcccaaaagu uaaacaaugg   1980
ccauugacag aagaaaaaau aaaagcauua guagaaauuu guacagaaau ggaaaaggaa   2040
gggaaaauuu caaaaauugg gccugagaau ccauacaaua cuccaguauu ugccauaaag   2100
aaaaaagaca guacuaaaug gagaaaauua guagauuuca gagaacuuaa uaagagaacu   2160
caagacuucu gggaaguuca auuaggaaua ccacaucccg caggguuaaa aaagaaaaaa   2220
ucaguaacag uacuggaugu gggugaugca uauuuuucag uucccuuaga ugaagacuuc   2280
aggaaguaua cugcauuuac cauaccuagu auaaacaaug agacaccagg gauuagauau   2340
caguacaaug ugcuuccaca gggauggaaa ggaucaccag caauauucca aaguagcaug   2400
acaaaaaucu uagagccuuu uaaaaaacaa aauccagaca uaguuaucua ucaauacaug   2460
gaugauuugu auguaggauc ugacuuagaa auagggcagc auagaacaaa aauagaggag   2520
cugagacaac aucuguugag guggggacuu accacaccag acaaaaaaca ucagaaagaa   2580
ccuccauucc uuuggauggg uuaugaacuc cauccugaua aauggacagu acagccuaua   2640
gugcugccag aaaaagacag cuggacuguc aaugacauac agaaguuagu ggggaaauug   2700
aauugggcaa gucagauuua cccagggauu aaaguaaggc aauuauguaa acuccuuaga   2760
ggaaccaaag cacuaacaga aguaauacca cuaacagaag aagcagagcu agaacuggca   2820
gaaaacagag agauucuaaa agaaccagua cauggagugu auuaugaccc aucaaaagac   2880
uuaauagcag aaauacagaa gcaggggcaa ggccaaugga cauaucaaau uuaucaagag   2940
ccauuuaaaa aucugaaaac aggaaaauau gcaagaauga ggggugccca cacuaaugau   3000
guaaaacaau uaacagaggc agugcaaaaa auaaccacag aaagcauagu aauaugggga   3060
aagacuccua aauuuaaacu acccauacaa aaggaaacau gggaaacaug guggacagag   3120
uauuggcaag ccaccuggau uccugagugg gaguuuguua auaccccucc uuuagugaaa   3180
uuaugguacc aguuagagaa agaacccaua guaggagcag aaaccuucua uguagauggg   3240
gcagcuaaca gggagacuaa auuaggaaaa gcaggauaug uuacuaacaa aggaagacaa   3300
aagguugucc cccuaacuaa cacaacaaau cagaaaacug aguuacaagc aauuuaucua   3360
gcuuugcagg auucaggauu agaaguaaac auaguaacag acucacaaua ugcauuagga   3420
aucauucaag cacaaccaga uaaaagugaa ucagaguuag ucaaucaaau aauagagcag   3480
uuaauaaaaa aggaaaaggu cuaucuggca uggguaccag cacacaaagg aauuggagga   3540
```

-continued

```
aaugaacaag uagauaaauu agucagugcu ggaaucagga aaauacuauu uuuagaugga   3600
auagauaagg cccaagauga acaugagaaa uaucacagua auuggagagc aauggcuagu   3660
gauuuuaacc ugccaccugu aguagcaaaa gaaauaguag ccagcuguga uaaaugucag   3720
cuaaaaggag aagccaugca uggacaagua gacuguaguc caggaauaug gcaacuagau   3780
uguacacauu uagaaggaaa aguuauccug guagcaguuc auguagccag uggauauaua   3840
gaagcagaag uuauuccagc agaaacaggg caggaaacag cauauuuucu uuuaaaauua   3900
gcaggaagau ggccaguaaa aacaauacau acagacaaug gcagcaauuu caccagugcu   3960
acgguuaagg ccgccuguug gugggcggga aucaagcagg aauuuggaau ucccuacaau   4020
ccccaaaguc aaggaguagu agaaucuaug aauaaagaau uaaagaaaau uauaggacag   4080
guaagagauc aggcugaaca ucuuaagaca gcaguacaaa uggcaguauu cauccacaau   4140
uuuaaaagaa aaggggggau ugggggguac agugcagggg aaagaauagu agacauaaua   4200
gcaacagaca uacaaacuaa agaauuacaa aaacaaauua caaaaauuca aaauuuucgg   4260
guuuauuaca gggacagcag aaauccacuu uggaaaggac cagcaaagcu ccucuggaaa   4320
ggugaagggg caguaguaau acaagauaau agugacauaa aaguagugcc aagaagaaaa   4380
gcaaagauca uuagggauua uggaaaacag auggcaggug augauugugu ggcaaguaga   4440
caggaugagg auuagaacau ggaaaaguuu aguaaaacac cauauguaug uuucagggaa   4500
agcuagggga ugguuuuaua gacaucacua ugaaagcccu cauccaagaa uaaguucaga   4560
aguacacauc ccacuagggg augcuagauu gguaauaaca acauauuggg gucugcauac   4620
aggagaaaga gacuggcauu ugggucaggg agucuccaua gaauggagga aaaagagaua   4680
uagcacacaa guagacccug aacuagcaga ccaacuaauu caucuguauu acuuugacug   4740
uuuuucagac ucugcuauaa gaaaggccuu auuaggacac auaguuagcc cuagguguga   4800
auaucaagca ggacauaaca agguaggauc ucuacaauac uuggcacuag cagcauuaau   4860
aacaccaaaa aagauaaagc caccuuugcc uaguguuacg aaacugacag aggauagaug   4920
gaacaagccc cagaagacca agggccacag agggagccac acaaugaaug gacacuagag   4980
cuuuuagagg agcuuaagaa ugaagcuguu agacauuuuc cuaggauuug gcuccauggc   5040
uuagggcaac auaucuauga aacuuauggg gauacuuggg caggagugga agccauaaua   5100
agaauucugc aacaacugcu guuuauccau uuucagaauu gggugucgac auagcagaau   5160
aggcguuacu cgacagagga gagcaagaaa uggagccagu agauccuaga cuagagcccu   5220
ggaagcaucc aggaagucag ccuaaaacug cuuguaccaa uugcuauugu aaaaaguguu   5280
gcuuucauug ccaaguuugu uucauaacaa aagccuuagg caucuccuau ggcaggaaga   5340
agcggagaca gcgacgaaga ccuccucaag gcagucagac ucaucaaguu ucucuaucaa   5400
agcaguaagu aguacaugua augcaaccua uacaaauagc aauaguagca uuaguaguag   5460
caauaauaau agcaauaguu guguggucca uaguaaucau agaauauagg aaaauauuaa   5520
gacaaagaaa aauagacagg uuaauugaua gacuaauaga aagagcagaa gacaguggca   5580
augagaguga aggagaaaua ucagcacuug uggagauggg gguggagaug gggcaccaug   5640
cuccuuggga uguugaugau cuguagugcu acagaaaaau ugugggucac agucuauuau   5700
gggguaccug uguggaagga agcaaccacc acucuauuuu gugcaucaga ugcuaaagca   5760
uaugauacag agguacauaa uguuugggcc acacaugccu guguacccac agaccccaac   5820
ccacaagaag uaguauuggu aaaugugaca gaaaauuuua acauguggaa aaaugacaug   5880
```

-continued

```
guagaacaga ugcaugagga uauaaucagu uuaugggauc aaagccuaaa gccaugugua   5940
aaauuaaccc cacucugugu uaguuuaaag ugcacugauu ugaagaauga uacuaauacc   6000
aauaguagua gcgggagaau gauaauggag aaaggagaga uaaaaaacug cucuuucaau   6060
aucagcacaa gcauaagagg uaaggugcag aaagaauaug cauuuuuuua uaaacuugau   6120
auaauaccaa uagauaauga uacuaccagc uauacguuga caaguuguaa caccucaguc   6180
auuacacagg ccuguccaaa gguauccuuu gagccaauuc ccauacauua uugugccccg   6240
gcugguuuug cgauucuaaa auguaauaau aagacguuca auggaacagg accauguaca   6300
aaugucagca caguacaaug uacacaugga auuaggccag uaguaucaac ucaacugcug   6360
uuaaauggca gucuggcaga agaagaggua guaauuagau cugccaauuu cacagacaau   6420
gcuaaaacca uaauaguaca gcugaaccaa ucuguagaaa uuaauuguac aagacccaac   6480
aacaauacaa gaaaaaguau ccguauccag agaggaccag ggagagcauu uguuacaaua   6540
ggaaaaauag gaaauaugag acaagcacau uguaacauua guagagcaaa auggaauaac   6600
acuuuaaaac agauagauag caaauuaaga gaacaauuug gaaauaauaa aacaauaauc   6660
uuuaagcagu ccucaggagg ggacccagaa auuguaacgc acaguuuuaa uuguggaggg   6720
gaauuuuucu acuguaauuc aacacaacug uuuaauagua cuugguuuaa uaguacuugg   6780
aguacuaaag ggucaaauaa cacugaagga agugacacaa ucacccuccc augcagaaua   6840
aaacaaauua uaaacaugug gcaggaagua ggaaaagcaa uguaugcccc ucccaucagu   6900
ggacaaauua gauguucauc aaauauuaca gggcugcuau uaacaagaga ugguggguaau   6960
agcaacaaug aguccgagau cuucagaccu ggaggaggag auaugaggga caauuggaga   7020
agugaauuau auaaauauaa aguaguaaaa auugaaccau uaggaguagc acccaccaag   7080
gcaaagagaa gaguggugca gagagaaaaa agagcagugg gaauaggagc uuuguuccuu   7140
ggguucuugg gagcagcagg aagcacuaug ggcgcagcgu caaugacgcu gacgguacag   7200
gccagacaau uauugucugg uauagugcag cagcagaaca auuugcugag ggcuauugag   7260
gcgcaacagc aucuguugca acucacaguc uggggcauca agcagcucca ggcaagaauc   7320
cuggcugugg aaagauaccu aaaggaucaa cagcuccugg ggauuugggg uugcucugga   7380
aaacucauuu gcaccacugc ugugccuugg aaugcuaguu ggaguaauaa aucucuggaa   7440
cagauuugga auaacaugac cuggauggag ugggacagag aaauuaacaa uuacacaagc   7500
uuaauacacu ccuuaauuga agaaucgcaa aaccagcaag aaaagaauga acaagaauua   7560
uuggaauuag auaaaugggc aaguuugugg aauugguuua acauaacaaa uuggcugugg   7620
uauauaaaau uauucauaau gauaguagga ggcuugguag guuuaagaau aguuuuugcu   7680
guacuuucug uagugaauag aguuaggcag ggauauucac cauuaucguu ucagacccac   7740
cucccaaucc cgaggggacc cgacaggccc gaaggaauag aagaagaagg uggagagaga   7800
gacagagaca gauccauucg auuagugaac ggauccuuag cacuuaucug ggacgaucug   7860
cggagccugu gccucuucag cuaccaccgc uugagagacu uacucuugau uguaacgagg   7920
auuguggaac uucugggacg caggggggugg gaagcccuca aauauuggug gaaucuccua   7980
caguauugga gucaggagcu aaagaauagu gcuguuagcu ugcucaaugc cacagcuaua   8040
gcaguagcug aggggacaga uaggguuaua gaaguaguac aaggagcuua uagagcuauu   8100
cgccacauac cuagaagaau aagacagggc uuggaaagga uuuugcuaua agaugggugg   8160
caagugguca aaaaguagug ugguuggaug gccugcugua agggaaagaa ugagacgagc   8220
ugagccagca gcagaugggg ugggagcagc aucucgagac cuagaaaaac auggagcaau   8280
```

-continued cacaaguagc aacacagcag cuaacaaugc ugauugugcc uggcuagaag cacaagagga 8340
ggaggaggug gguuuuccag ucacaccuca gguaccuuua agaccaauga cuuacaaggc 8400
agcuguagau cuuagccacu uuuuaaaaga aaaggggga cuggaagggc uaauucacuc 8460
ccaacgaaga caagauaucc uugaucugug gaucuaccac acacaaggcu acuucccuga 8520
uuagcagaac uacacaccag ggccagggau cagauaucca cugaccuuug gauggugcua 8580
caagcuagua ccaguugagc cagagaaguu agaagaagcc aacaaaggag agaacaccag 8640
cuuguuacac ccugugagcc ugcauggaau ggaugacccg gagagagaag uguuagagug 8700
gagguuugac agccgccuag cauuucauca cauggcccga gagcugcauc cggaguacuu 8760
caagaacugc ugacaucgag cuugcuacaa gggacuuucc gcuggggacu uuccagggag 8820
gcguggccug ggcgggacug gggaguggcg agcccucaga uccugcauau aagcagcugc 8880
uuuuugccug uacugggucu cucugguuag accagaucug agccugggag cuc 8933

<210> SEQ ID NO 4
<211> LENGTH: 8933
<212> TYPE: RNA
<213> ORGANISM: Artificial Sequence
<220> FEATURE:
<223> OTHER INFORMATION: Sequence of the IAC-Asrc pseudo target
<221> NAME/KEY: mutation
<222> LOCATION: (4135)...(4155)
<223> OTHER INFORMATION: Mutated positions: 4135, 4140-1, 4145, 4150,
4152-3, 4155

<400> SEQUENCE: 4
gagcucucuc gacgcaggac ucggcuugcu gaagcgcgca cggcaagagg cgaggggcgg 60
cgacugguga guacgccaaa aauuuugacu agcggaggcu agaaggagag agaugggugc 120
gagagcguca guauuaagcg ggggagaauu agaucgaugg gaaaaaauuc gguuaaggcc 180
agggggaaag aaaaaauaua aauuaaaaca uauaguaugg gcaagcaggg agcuagaacg 240
auucgcaguu aauccuggcc uguuagaaac aucagaaggc uguagacaaa uacugggaca 300
gcuacaacca ucccuucaga caggaucaga agaacuuaga ucauuauaua auacaguagc 360
aacccucuau ugugugcauc aaaggauaga gauaaaagac accaaggaag cuuuagacaa 420
gauagaggaa gagcaaaaca aaaguaagaa aaaagcacag caagcagcag cugacacagg 480
acacagcagu caggucagcc aaaauuaccc uauagugcag aacauccagg ggcaaauggu 540
acaucaggcc auaucaccua gaacuuuaaa ugcaugggua aaaguaguag aagagaaggc 600
uuucagccca gaaguaauac ccauguuuuc agcauuauca gaaggagcca ccccacaaga 660
uuuaaacacc augcuaaaca caguggggggg acaucaagca gccaugcaaa uguuaaaaga 720
gaccaucaau gaggaagcug cagaauggga uagaguacau ccagugcaug cagggccuau 780
ugcaccaggc cagaugagag aaccaagggg aagugacaua gcaggaacua cuaguacccu 840
ucaggaacaa auaggaugga ugacaaauaa uccaccuauc ccaguaggag aaauuuauaa 900
aagauggaua auccugggau uaaauaaaau aguaagaaug uauagcccua ccagcauucu 960
ggacauaaga caaggaccaa aagaaccuuu uagagacuau guagaccggu ucuauaaaac 1020
ucuaagagcc gagcaagcuu cacaggaggu aaaaaauugg augacagaaa ccuuguuggu 1080
ccaaaaugcg aacccagauu guaagacuau uuuaaaagca uugggaccag cggcuacacu 1140
agaagaaaug augacagcau gucagggagu aggaggaccc ggccauaagg caagaguuuu 1200
ggcugaagca augagccaag uaacaaauac agcuaccaua augaugcaga gaggcaauuu 1260

-continued

```
uaggaaccaa agaaagaugg uuaaguguuu caauuguggc aaagaagggc acacagccag   1320
aaauugcagg gccccuagga aaaagggcug uuggaaaugu ggaaaggaag gacaccaaau   1380
gaaagauugu acugagagac aggcuaauuu uuuagggaag aucuggccuu ccuacaaggg   1440
aaggccaggg aauuuucuuc agagcagacc agagccaaca gccccaccau uucuucagag   1500
cagaccagag ccaacagccc caccagaaga gagcuucagg ucugggguag agacaacaac   1560
ucccccucag aagcaggagc cgauagacaa ggaacuguau ccuuuaacuu cccucagauc   1620
acucuuuggc aacgaccccu cgucacaaua aagauagggg ggcaacuaaa ggaagcucua   1680
uuagauacag gagcagauga uacaguauua gaagaaauga guuugccagg aagauggaaa   1740
ccaaaaauga uagggggaau uggagguuuu aucaaaguaa gacaguauga ucagauacuc   1800
auagaaaucu guggacauaa agcuauaggu acaguauuag uaggaccuac accugucaac   1860
auaauuggaa gaaaucuguu gacucagauu gguugcacuu uaaauuuucc cauuagcccu   1920
auugagacug uaccaguaaa auuaaagcca ggaauggaug gcccaaaagu uaaacaaugg   1980
ccauugacag aagaaaaaau aaaagcauua guagaaauuu guacagaaau ggaaaaggaa   2040
gggaaaauuu caaaaauugg gccugagaau ccauacaaua cuccaguauu ugccauaaag   2100
aaaaaagaca guacuaaaug gagaaaauua guagauuuca gagaacuuaa uaagagaacu   2160
caagacuucu gggaaguuca auuaggaaua ccacaucccg caggguuaaa aaagaaaaaa   2220
ucaguaacag uacuggaugu gggugaugca uauuuuucag uucccuuaga ugaagacuuc   2280
aggaaguaua cugcauuuac cauaccuagu auaaacaaug agacaccagg gauuagauau   2340
caguacaaug ugcuuccaca gggauggaaa ggaucaccag caauauucca aaguagcaug   2400
acaaaaaucu uagagccuuu uaaaaaacaa aauccagaca uaguuaucua ucaauacaug   2460
gaugauuugu auguaggauc ugacuuagaa auagggcagc auagaacaaa aauagaggag   2520
cugagacaac aucuguugag gugggacuu accacaccag acaaaaaaca ucagaaagaa   2580
ccuccauucc uuuggauggg uuaugaacuc cauccugaua aauggacagu acagccuaua   2640
gugcugccag aaaaagacag cuggacuguc aaugacauac agaaguuagu ggggaaauug   2700
aauugggcaa gucagauuua cccagggauu aaaguaaggc aauuauguaa acuccuuaga   2760
ggaaccaaag cacuaacaga aguaauacca cuaacagaag aagcagagcu agaacuggca   2820
gaaaacagag agauucuaaa agaaccagua cauggagugu auuaugaccc aucaaaagac   2880
uuaauagcag aaauacagaa gcaggggcaa ggccaaugga cauaucaaau uuaucaagag   2940
ccauuuaaaa aucugaaaac aggaaaauau gcaagaauga ggggugccca cacuaaugau   3000
guaaaacaau uaacagaggc agugcaaaaa auaaccacag aaagcauagu aauaugggga   3060
aagacuccua aauuuaaacu acccauacaa aaggaaacau gggaaacaug guggacagag   3120
uauuggcaag ccaccuggau uccugagugg gaguuuguua auaccccucc uuuagugaaa   3180
uuaugguacc aguuagagaa agaacccaua guaggagcag aaaccuucua uguagauggg   3240
gcagcuaaca gggagacuaa auuaggaaaa gcaggauaug uuacuaacaa aggaagacaa   3300
aagguugucc cccuaacuaa cacaacaaau cagaaaacug aguuacaagc aauuuaucua   3360
gcuuugcagg auucaggauu agaaguaaac auaguaacag acucacaaua ugcauuagga   3420
aucauucaag cacaaccaga uaaaagugaa ucagaguuag ucaaucaaau aauagagcag   3480
uuaauaaaaa aggaaaaggu cuaucuggca ugguuaccag cacacaaagg aauuggagga   3540
aaugaacaag uagauaaauu agucagugcu ggaaucagga aaauacuauu uuuagaugga   3600
auagauaagg cccaagauga acaugagaaa uaucacagua auuggagagc aauggcuagu   3660
```

-continued

```
gauuuuaacc ugccaccugu aguagcaaaa gaaauaguag ccagcuguga uaaaugucag   3720
cuaaaaggag aagccaugca uggacaagua gacuguaguc caggaauaug gcaacuagau   3780
uguacacauu uagaaggaaa aguuauccug guagcaguuc auguagccag uggauauaua   3840
gaagcagaag uuauuccagc agaaacaggg caggaaacag cauauuuucu uuuaaaauua   3900
gcaggaagau ggccaguaaa aacaauacau acagacaaug gcagcaauuu caccagugcu   3960
acgguuaagg ccgccuguug gugggcggga aucaagcagg aauuuggaau ucccuacaau   4020
ccccaaaguc aaggaguagu agaaucuaug aauaaagaau uaaagaaaau uauaggacag   4080
guaagagauc aggcugaaca ucuuaagaca gcaguacaaa uggcaguauu caucuacaag   4140
cuuagaagau agagagggau ugggggguac agugcagggg aaagaauagu agacauaaua   4200
gcaacagaca uacaaacuaa agaauuacaa aaacaaauua caaaaauuca aaauuuucgg   4260
guuuauuaca gggacagcag aaauccacuu uggaaaggac cagcaaagcu ccucuggaaa   4320
ggugaagggg caguaguaau acaagauaau agugacauaa aaguagugcc aagaagaaaa   4380
gcaaagauca uuagggauua uggaaaacag auggcaggug augauugugu ggcaaguaga   4440
caggaugagg auuagaacau ggaaaaguuu aguaaaacac cauauguaug uuucagggaa   4500
agcuagggga ugguuuuaua gacaucacua ugaaagcccu cauccaagaa uaaguucaga   4560
aguacacauc ccacuagggg augcuagauu gguaauaaca acauauuggg gucugcauac   4620
aggagaaaga gacuggcauu ugggucaggg agucuccaua gaauggagga aaaagagaua   4680
uagcacacaa guagacccug aacuagcaga ccaacuaauu caucuguauu acuuugacug   4740
uuuuucagac ucugcuauaa gaaaggccuu auuaggacac auaguuagcc cuaggugu ga   4800
auaucaagca ggacauaaca agguaggauc ucuacaauac uuggcacuag cagcauuaau   4860
aacaccaaaa aagauaaagc caccuuugcc uaguguuacg aaacugacag aggauagaug   4920
gaacaagccc cagaagacca agggccacag agggagccac acaaugaaug gacacuagag   4980
cuuuuagagg agcuuaagaa ugaagcuguu agacauuuuc cuaggauuug gcuccauggc   5040
uuagggcaac auaucuauga aacuuauggg gauacuuggg caggagugga agccauaaua   5100
agaauucugc aacaacugcu guuuauccau uuucagaauu gggugucgac auagcagaau   5160
aggcguuacu cgacagagga gagcaagaaa uggagccagu agauccuaga cuagagcccu   5220
ggaagcaucc aggaagucag ccuaaaacug cuuguaccaa uugcuauugu aaaaaguguu   5280
gcuuucauug ccaaguuugu uucauaacaa aagccuuagg caucuccuau ggcaggaaga   5340
agcggagaca gcgacgaaga ccuccucaag gcagucagac ucaucaaguu ucucuaucaa   5400
agcaguaagu aguacaugua augcaaccua uacaaauagc aauaguagca uuaguaguag   5460
caauaauaau agcaauaguu guguggucca uaguaaucau agaauauagg aaaauauuaa   5520
gacaaagaaa aauagacagg uuaauugaua gacuaauaga aagagcagaa gacaguggca   5580
augagaguga aggagaaaua ucagcacuug uggagauggg gguggagaug gggcaccaug   5640
cuccuuggga uguugaugau cuguagugcu acagaaaaau ugugggucac agucuauuau   5700
gggguaccug uguggaagga agcaaccacc acucuauuuu gugcaucaga ugcuaaagca   5760
uaugauacag agguacauaa uguuugggcc acacaugccu guguacccac agaccccaac   5820
ccacaagaag uaguauuggu aaaugugaca gaaaauuuua acauguggaa aaaugacaug   5880
guagaacaga ugcaugagga uauaaucagu uuaugggauc aaagccuaaa gccaugugua   5940
aaauuaaccc cacucugugu uaguuuaaag ugcacugauu ugaagaauga uacuaauacc   6000
```

-continued

```
aauaguagua gcgggagaau gauaauggag aaaggagaga uaaaaaacug cucuuucaau   6060
aucagcacaa gcauaagagg uaaggugcag aaagaauaug cauuuuuuua uaaacuugau   6120
auaauaccaa uagauaauga uacuaccagc uauacguuga caaguuguaa caccucaguc   6180
auuacacagg ccuguccaaa gguauccuuu gagccaauuc ccauacauua uugugccccg   6240
gcugguuuug cgauucuaaa auguaauaau aagacguuca auggaacagg accauguaca   6300
aaugucagca caguacaaug uacacaugga auuaggccag uaguaucaac ucaacugcug   6360
uuaaauggca gucuggcaga agaagaggua guaauuagau cugccaauuu cacagacaau   6420
gcuaaaacca uaauaguaca gcugaaccaa ucuguagaaa uuaauuguac aagacccaac   6480
aacaauacaa gaaaaaguau ccguauccag agaggaccag ggagagcauu uguuacaaua   6540
ggaaaaauag gaaauaugag acaagcacau uguaacauua guagagcaaa auggaauaac   6600
acuuuaaaac agauagauag caaauuaaga gaacaauuug gaaauaauaa aacaauaauc   6660
uuuaagcagu ccucaggagg ggacccagaa auuguaacgc acaguuuuaa uuguggaggg   6720
gaauuuuucu acuguaauuc aacacaacug uuuaauagua cuugguuuaa uaguacuugg   6780
aguacuaaag ggucaaauaa cacugaagga agugacacaa ucacccuccc augcagaaua   6840
aaacaaauua uaaacaugug gcaggaagua ggaaaagcaa uguaugcccc ucccaucagu   6900
ggacaaauua gauguucauc aaauauuaca gggcugcuau uaacaagaga uggugguaau   6960
agcaacaaug aguccgagau cuucagaccu ggaggaggag auaugaggga caauuggaga   7020
agugaauuau auaaauauaa aguaguaaaa auugaaccau uaggaguagc acccaccaag   7080
gcaaagagaa gaguggugca gagagaaaaa agagcagugg gaauaggagc uuuguuccuu   7140
ggguucuugg gagcagcagg aagcacuaug ggcgcagcgu caaugacgcu gacgguacag   7200
gccagacaau uauugucugg uauagugcag cagcagaaca auuugcugag ggcuauugag   7260
gcgcaacagc aucuguugca acucacaguc uggggcauca agcagcucca ggcaagaauc   7320
cuggcugugg aaagauaccu aaaggaucaa cagcuccugg ggauuugggg uugcucugga   7380
aaacucauuu gcaccacugc ugugccuugg aaugcuaguu ggaguaauaa aucucuggaa   7440
cagauuugga auaacaugac cuggauggag ugggacagag aaauuaacaa uuacacaagc   7500
uuaauacacu ccuuaauuga agaaucgcaa aaccagcaag aaaagaauga acaagaauua   7560
uuggaauuag auaaaugggc aaguuugugg aauugguuua acauaacaaa uuggcugugg   7620
uauauaaaau uauucauaau gauaguagga ggcuugguag guuuaagaau aguuuuugcu   7680
guacuuucug uagugaauag aguuaggcag ggauauucac cauuaucguu ucagacccac   7740
cucccaaucc cgaggggacc cgacaggccc gaaggaauag aagaagaagg uggagagaga   7800
gacagagaca gauccauucg auuagugaac ggauccuuag cacuuaucug ggacgaucug   7860
cggagccugu gccucuucag cuaccaccgc uugagagacu uacucuugau uguaacgagg   7920
auuguggaac uucugggacg cagggggugg gaagcccuca aauauuggug gaaucuccua   7980
caguauugga gucaggagcu aaagaauagu gcuguuagcu ugcucaaugc cacagcuaua   8040
gcaguagcug aggggacaga uaggguuaua gaaguaguac aaggagcuua uagagcuauu   8100
cgccacauac cuagaagaau aagacagggc uuggaaagga uuuugcuaua agaugggugg   8160
caagugguca aaaaguagug ugguuggaug gccugcugua agggaaagaa ugagacgagc   8220
ugagccagca gcagaugggg ugggagcagc aucucgagac cuagaaaaac auggagcaau   8280
cacaaguagc aacacagcag cuaacaaugc ugauugugcc uggcuagaag cacaagagga   8340
ggaggaggug gguuuuccag ucacaccuca gguaccuuua agaccaauga cuuacaaggc   8400
```

-continued agcuguagau cuuagccacu uuuuaaaaga aaaggggga cuggaagggc uaauucacuc 8460
ccaacgaaga caagauaucc uugaucugug gaucuaccac acacaaggcu acuucccuga 8520
uuagcagaac uacacaccag ggccagggau cagauaucca cugaccuuug gauggugcua 8580
caagcuagua ccaguugagc cagagaaguu agaagaagcc aacaaaggag agaacaccag 8640
cuuguuacac ccugugagcc ugcauggaau ggaugacccg gagagagaag uguuagagug 8700
gagguuugac agccgccuag cauuucauca cauggcccga gagcugcauc cggaguacuu 8760
caagaacugc ugacaucgag cuugcuacaa gggacuuucc gcuggggacu uuccagggag 8820
gcguggccug ggcgggacug gggaguggcg agcccucaga uccugcauau aagcagcugc 8880
uuuuugccug uacugggucu cucugguuag accagaucug agccugggag cuc 8933

<210> SEQ ID NO 5
<211> LENGTH: 30
<212> TYPE: DNA
<213> ORGANISM: HIV
<220> FEATURE:
<221> NAME/KEY: source
<222> LOCATION: (1)...(30)
<223> OTHER INFORMATION: Sequence of AE(+)4134 HIV-specific probe.

<400> SEQUENCE: 5
ccacaatttt aaaagaaaag gggggattgg 30

<210> SEQ ID NO 6
<211> LENGTH: 67
<212> TYPE: DNA
<213> ORGANISM: Artificial Sequence
<220> FEATURE:
<223> OTHER INFORMATION: Sequence of (-)3837 A30 capture probe.

<400> SEQUENCE: 6
ccctgtttct gctggaataa cttctgcttc tatatttaaa aaaaaaaaaa aaaaaaaaaa 60
aaaaaaa 67

<210> SEQ ID NO 7
<211> LENGTH: 57
<212> TYPE: DNA
<213> ORGANISM: Artificial Sequence
<220> FEATURE:
<223> OTHER INFORMATION: Sequence of the (-)4258 A30 capture probe.

<400> SEQUENCE: 7
tctgctgtcc ctgtaataaa cccgtttaaa aaaaaaaaaa aaaaaaaaaa aaaaaaa 57

<210> SEQ ID NO 8
<211> LENGTH: 22
<212> TYPE: DNA
<213> ORGANISM: HIV
<220> FEATURE:
<221> NAME/KEY: source
<222> LOCATION: (0)...(0)
<223> OTHER INFORMATION: Sequence of the AE(+)4134b probe

<400> SEQUENCE: 8
ccacaatttt aaaagaaaag gg 22

<210> SEQ ID NO 9
<211> LENGTH: 8933
<212> TYPE: RNA
<213> ORGANISM: Artificial Sequence
<220> FEATURE:

-continued

<223> OTHER INFORMATION: Sequence of the IAC-Bscr pseudo target
<221> NAME/KEY: mutation
<222> LOCATION: (4140)...(4159)
<223> OTHER INFORMATION: Mutated positions: 4140-42, 4145-47, 4152,
4156-57, 4159

<400> SEQUENCE: 9

```
gagcucucuc gacgcaggac ucggcuugcu gaagcgcgca cggcaagagg cgaggggcgg     60
cgacugguga guacgccaaa aauuuugacu agcggaggcu agaaggagag agaugggugc    120
gagagcguca guauuaagcg ggggagaauu agaucgaugg gaaaaaauuc gguuaaggcc    180
agggggaaag aaaaaauaua aauuaaaaca uauaguaugg gcaagcaggg agcuagaacg    240
auucgcaguu aauccuggcc uguuagaaac aucagaaggc uguagacaaa uacugggaca    300
gcuacaacca ucccuucaga caggaucaga agaacuuaga ucauuauaua auacaguagc    360
aacccucuau ugugugcauc aaaggauaga gauaaaagac accaaggaag cuuuagacaa    420
gauagaggaa gagcaaaaca aaaguaagaa aaaagcacag caagcagcag cugacacagg    480
acacagcagu caggucagcc aaaauuaccc uauagugcag aacauccagg ggcaaauggu    540
acaucaggcc auaucaccua gaacuuuaaa ugcaugggua aaaguaguag aagagaaggc    600
uuucagccca gaaguaauac ccauguuuuc agcauuauca gaaggagcca ccccacaaga    660
uuuaaacacc augcuaaaca caguggggggg acaucaagca gccaugcaaa uguuaaaaga    720
gaccaucaau gaggaagcug cagaauggga uagaguacau ccagugcaug cagggccuau    780
ugcaccaggc cagaugagag aaccaagggg aagugacaua gcaggaacua cuaguacccu    840
ucaggaacaa auaggaugga ugacaaauaa uccaccuauc ccaguaggag aaauuuauaa    900
aagauggaua auccugggau uaaauaaaau aguaagaaug uauagcccua ccagcauucu    960
ggacauaaga caaggaccaa aagaaccuuu uagagacuau guagaccggu ucuauaaaac   1020
ucuaagagcc gagcaagcuu cacaggaggu aaaaaauugg augacagaaa ccuuguuggu   1080
ccaaaaugcg aacccagauu guaagacuau uuuaaaagca uugggaccag cggcuacacu   1140
agaagaaaug augacagcau gucagggagu aggaggaccc ggccauaagg caagaguuuu   1200
ggcugaagca augagccaag uaacaaauac agcuaccaua augaugcaga gaggcaauuu   1260
uaggaaccaa agaaagaugg uuaaguguuu caauuguggc aaagaagggc acacagccag   1320
aaauugcagg gccccuagga aaaagggcug uuggaaaugu ggaaaggaag gacaccaaau   1380
gaaagauugu acugagagac aggcuaauuu uuuagggaag aucuggccuu ccuacaaggg   1440
aaggccaggg aauuuucuuc agagcagacc agagccaaca gccccaccau uucuucagag   1500
cagaccagag ccaacagccc caccagaaga gagcuucagg ucugggguag agacaacaac   1560
ucccccucag aagcaggagc cgauagacaa ggaacuguau ccuuuaacuu cccucagauc   1620
acucuuuggc aacgaccccu cgucacaaua aagauagggg ggcaacuaaa ggaagcucua   1680
uuagauacag gagcagauga uacaguauua gaagaaauga guuugccagg aagauggaaa   1740
ccaaaaauga uagggggaau uggagguuuu aucaaaguaa gacaguauga ucagauacuc   1800
auagaaaucu guggacauaa agcuauaggu acaguauuag uaggaccuac accugucaac   1860
auaauuggaa gaaaucuguu gacucagauu gguugcacuu uaaauuuucc cauuagcccu   1920
auugagacug uaccaguaaa auuaaagcca ggaauggaug gcccaaaagu uaaacaaugg   1980
ccauugacag aagaaaaaau aaaagcauua guagaaauuu guacagaaau ggaaaaggaa   2040
gggaaaauuu caaaaauugg gccugagaau ccauacaaua cuccaguauu ugccauaaag   2100
aaaaaagaca guacuaaaug gagaaaauua guagauuuca gagaacuuaa uaagagaacu   2160
```

-continued

```
caagacuucu gggaaguuca auuaggaaua ccacaucccg cagguuaaa aaagaaaaaa   2220
ucaguaacag uacuggaugu gggugaugca uauuuuucag uucccuuaga ugaagacuuc   2280
aggaaguaua cugcauuuac cauaccuagu auaaacaaug agacaccagg gauuagauau   2340
caguacaaug ugcuuccaca gggauggaaa ggaucaccag caauauucca aaguagcaug   2400
acaaaaaucu uagagccuuu uaaaaaacaa aauccagaca uaguuaucua ucaauacaug   2460
gaugauuugu auguaggauc ugacuuagaa auagggcagc auagaacaaa aauagaggag   2520
cugagacaac aucuguugag gugggacuu accacaccag acaaaaaaca ucagaaagaa   2580
ccuccauucc uuuggauggg uuaugaacuc cauccugaua aauggacagu acagccuaua   2640
gugcugccag aaaaagacag cuggacuguc aaugacauac agaaguuagu ggggaaauug   2700
aauugggcaa gucagauuua cccagggauu aaaguaaggc aauuauguaa acuccuuaga   2760
ggaaccaaag cacuaacaga aguaauacca cuaacagaag aagcagagcu agaacuggca   2820
gaaaacagag agauucuaaa agaaccagua cauggagugu auuaugaccc aucaaaagac   2880
uuaauagcag aaauacagaa gcaggggcaa ggccaaugga cauaucaaau uuaucaagag   2940
ccauuuaaaa aucugaaaac aggaaaauau gcaagaauga ggggugccca cacuaaugau   3000
guaaaacaau uaacagaggc agugcaaaaa auaaccacag aaagcauagu aauaugggga   3060
aagacuccua aauuuaaacu acccauacaa aaggaaacau gggaaacaug guggacagag   3120
uauuggcaag ccaccuggau uccugagugg gaguuuguua auaccccucc uuuagugaaa   3180
uuaugguacc aguuagagaa agaacccaua guaggagcag aaaccuucua uguagauggg   3240
gcagcuaaca gggagacuaa auuaggaaaa gcaggauaug uuacuaacaa aggaagacaa   3300
aagguugucc cccuaacuaa cacaacaaau cagaaaacug aguuacaagc aauuuaucua   3360
gcuuugcagg auucaggauu agaaguaaac auaguaacag acucacaaua ugcauuagga   3420
aucauucaag cacaaccaga uaaaagugaa ucagaguuag ucaaucaaau aauagagcag   3480
uuaauaaaaa aggaaaaggu cuaucuggca uggguaccag cacacaaagg aauuggagga   3540
aaugaacaag uagauaaauu agucagugcu ggaaucagga aaauacuauu uuuagaugga   3600
auagauaagg cccaagauga acaugagaaa uaucacagua auuggagagc aauggcuagu   3660
gauuuuaacc ugccaccugu aguagcaaaa gaaauaguag ccagcuguga uaaaugucag   3720
cuaaaaggag aagccaugca uggacaagua gacuguaguc caggaauaug gcaacuagau   3780
uguacacauu uagaaggaaa aguuauccug guagcaguuc auguagccag uggauauaua   3840
gaagcagaag uuauuccagc agaaacaggg caggaaacag cauauuuucu uuuaaaauua   3900
gcaggaagau ggccaguaaa aacaauacau acagacaaug gcagcaauuu caccagugcu   3960
acgguuaagg ccgccuguug gugggcggga aucaagcagg aauuuggaau ucccuacaau   4020
ccccaaaguc aaggaguagu agaaucuaug aauaaagaau uaaagaaaau uauaggacag   4080
guaagagauc aggcugaaca ucuuaagaca gcaguacaaa uggcaguauu cauccagaaa   4140
aauauuugaa aggggaagcu uggggggguac agugcagggg aaagaauagu agacauaaua   4200
gcaacagaca uacaaacuaa agaauuacaa aaacaaauua caaaaauuca aaauuuucgg   4260
guuuauuaca gggacagcag aaauccacuu uggaaaggac cagcaaagcu ccucuggaaa   4320
ggugaagggg caguaguaau acaagauaau agugacauaa aaguagugcc aagaagaaaa   4380
gcaaagauca uuagggauua uggaaaacag auggcaggug augauugugu ggcaaguaga   4440
caggaugagg auuagaacau ggaaaaguuu aguaaaacac cauauguaug uuucagggaa   4500
```

-continued agcuagggga ugguuuuaua gacaucacua ugaaagcccu cauccaagaa uaaguucaga 4560
aguacacauc ccacuagggg augcuagauu gguaauaaca acauauuggg gucugcauac 4620
aggagaaaga gacuggcauu ugggucaggg agucuccaua gaauggagga aaaagagaua 4680
uagcacacaa guagacccug aacuagcaga ccaacuaauu caucuguauu acuuugacug 4740
uuuuucagac ucugcuauaa gaaaggccuu auuaggacac auaguuagcc cuagguguga 4800
auaucaagca ggacauaaca agguaggauc ucuacaauac uuggcacuag cagcauuaau 4860
aacaccaaaa aagauaaagc caccuuugcc uaguguuacg aaacugacag aggauagaug 4920
gaacaagccc cagaagacca agggccacag agggagccac acaaugaaug gacacuagag 4980
cuuuuagagg agcuuaagaa ugaagcuguu agacauuuuc cuaggauuug gcuccauggc 5040
uuagggcaac auaucuauga aacuuauggg gauacuuggg caggagugga agccauaaua 5100
agaauucugc aacaacugcu guuuauccau uuucagaauu gggugucgac auagcagaau 5160
aggcguuacu cgacagagga gagcaagaaa uggagccagu agauccuaga cuagagcccu 5220
ggaagcaucc aggaagucag ccuaaaacug cuuguaccaa uugcuauugu aaaaaguguu 5280
gcuuucauug ccaaguuugu uucauaacaa aagccuuagg caucuccuau ggcaggaaga 5340
agcggagaca gcgacgaaga ccuccucaag gcagucagac ucaucaaguu ucucuaucaa 5400
agcaguaagu aguacaugua augcaaccua uacaaauagc aauaguagca uuaguaguag 5460
caauaauaau agcaauaguu guguggucca uaguaaucau agaauauagg aaaauauuaa 5520
gacaaagaaa aauagacagg uuaauugaua gacuaauaga aagagcagaa gacaguggca 5580
augagaguga aggagaaaua ucagcacuug uggagauggg gguggagaug gggcaccaug 5640
cuccuuggga uguugaugau cuguagugcu acagaaaaau ugugggucac agucuauuau 5700
gggguaccug uguggaagga agcaaccacc acucuauuuu gugcaucaga ugcuaaagca 5760
uaugauacag agguacauaa uguuugggcc acacaugccu guguacccac agaccccaac 5820
ccacaagaag uaguauuggu aaaugugaca gaaaauuuua acauguggaa aaaugacaug 5880
guagaacaga ugcaugagga uauaaucagu uuaugggauc aaagccuaaa gccaugugua 5940
aaauuaaccc cacucugugu uaguuuaaag ugcacugauu ugaagaauga uacuaauacc 6000
aauaguagua gcgggagaau gauaauggag aaaggagaga uaaaaaacug cucuuucaau 6060
aucagcacaa gcauaagagg uaaggugcag aaagaauaug cauuuuuuua uaaacuugau 6120
auaauaccaa uagauaauga uacuaccagc uauacguuga caaguuguaa caccucaguc 6180
auuacacagg ccuguccaaa gguauccuuu gagccaauuc ccauacauua uugugccccg 6240
gcugguuuug cgauucuaaa auguaauaau aagacguuca auggaacagg accauguaca 6300
aaugucagca caguacaaug uacacaugga auuaggccag uaguaucaac ucaacugcug 6360
uuaaauggca gucuggcaga agaagaggua guaauuagau cugccaauuu cacagacaau 6420
gcuaaaacca uaauaguaca gcugaaccaa ucuguagaaa uuaauuguac aagacccaac 6480
aacaauacaa gaaaaaguau ccguauccag agaggaccag ggagagcauu uguuacaaua 6540
ggaaaaauag gaaauaugag acaagcacau uguaacauua guagagcaaa auggaauaac 6600
acuuuaaaac agauagauag caaauuaaga gaacaauuug gaaauaauaa aacaauaauc 6660
uuuaagcagu ccucaggagg ggacccagaa auuguaacgc acaguuuuaa uuguggaggg 6720
gaauuuuucu acuguaauuc aacacaacug uuuaauagua cuugguuuaa uaguacuugg 6780
aguacuaaag ggucaaauaa cacugaagga agugacacaa ucacccuccc augcagaaua 6840
aaacaaauua uaaacaugug gcaggaagua ggaaaagcaa uguaugcccc ucccaucagu 6900

-continued

```
ggacaaauua gauguucauc aaauauuaca gggcugcuau uaacaagaga uggugguaau   6960

agcaacaaug aguccgagau cuucagaccu ggaggaggag auaugaggga caauuggaga   7020

agugaauuau auaaauauaa aguaguaaaa auugaaccau uaggaguagc acccaccaag   7080

gcaaagagaa gaguggugca gagagaaaaa agagcagugg gaauaggagc uuuguuccuu   7140

ggguucuugg gagcagcagg aagcacuaug ggcgcagcgu caaugacgcu gacgguacag   7200

gccagacaau uauugucugg uauagugcag cagcagaaca auuugcugag ggcuauugag   7260

gcgcaacagc aucuguugca acucacaguc uggggcauca agcagcucca ggcaagaauc   7320

cuggcugugg aaagauaccu aaaggaucaa cagcuccugg ggauuugggg uugcucugga   7380

aaacucauuu gcaccacugc ugugccuugg aaugcuaguu ggaguaauaa aucucuggaa   7440

cagauuugga auaacaugac cuggauggag ugggacagag aaauuaacaa uuacacaagc   7500

uuaauacacu ccuuaauuga agaaucgcaa aaccagcaag aaaagaauga acaagaauua   7560

uuggaauuag auaaaugggc aaguuugugg aauugguuua acauaacaaa uuggcugugg   7620

uauauaaaau uauucauaau gauaguagga ggcuugguag guuuaagaau aguuuuugcu   7680

guacuuucug uagugaauag aguuaggcag ggauauucac cauuaucguu ucagacccac   7740

cucccaaucc cgaggggacc cgacaggccc gaaggaauag aagaagaagg uggagagaga   7800

gacagagaca gauccauucg auuagugaac ggauccuuag cacuuaucug ggacgaucug   7860

cggagccugu gccucuucag cuaccaccgc uugagagacu uacucuugau uguaacgagg   7920

auuguggaac uucugggacg caggggggugg gaagcccuca aauauuggug gaaucuccua   7980

caguauugga gucaggagcu aaagaauagu gcuguuagcu ugcucaaugc cacagcuaua   8040

gcaguagcug aggggacaga uaggguuaua gaaguaguac aaggagcuua uagagcuauu   8100

cgccacauac cuagaagaau aagacagggc uuggaaagga uuuugcuaua agaugggugg   8160

caagugguca aaaaguagug ugguuggaug gccugcugua agggaaagaa ugagacgagc   8220

ugagccagca gcagaugggg ugggagcagc aucucgagac cuagaaaaac auggagcaau   8280

cacaaguagc aacacagcag cuaacaaugc ugauugugcc uggcuagaag cacaagagga   8340

ggaggaggug gguuuuccag ucacaccuca gguaccuuua agaccaauga cuuacaaggc   8400

agcuguagau cuuagccacu uuuuaaaaga aaaggggga cuggaagggc uaauucacuc   8460

ccaacgaaga caagauaucc uugaucugug gaucuaccac acacaaggcu acuucccuga   8520

uuagcagaac uacacaccag ggccagggau cagauaucca cugaccuuug gauggugcua   8580

caagcuagua ccaguugagc cagagaaguu agaagaagcc aacaaaggag agaacaccag   8640

cuuguuacac ccugugagcc ugcauggaau ggaugacccg gagagagaag uguuagagug   8700

gagguuugac agccgccuag cauuucauca cauggcccga gagcugcauc cggaguacuu   8760

caagaacugc ugacaucgag cuugcuacaa gggacuuucc gcuggggacu uuccagggag   8820

gcguggccug ggcgggacug gggaguggcg agcccucaga uccugcauau aagcagcugc   8880

uuuuugccug uacugggucu cucugguuag accagaucug agccugggag cuc          8933
```

POLYNUCLEOTIDE QUANTITATION METHOD

This application is a continuation of application Ser. No. 09/620,958, filed Jul. 21, 2000 now U.S. Pat. No. 6,294,338, which claims the benefit of U.S. Provisional Application No. 60/145,432, filed Jul. 23, 1999.

FIELD OF THE INVENTION

The present invention relates to methods and compositions useful for improving the precision and quantitative capacity of polynucleotide amplification reactions commonly performed in molecular genetics laboratories.

BACKGROUND OF THE INVENTION

Enzyme-based procedures for amplifying polynucleotides are now established tools for diagnostic, environmental and forensic testing. The market for DNA probe diagnostics in clinical laboratories now represents several hundred million dollars each year. The clinical diagnostics-probe business is expected to grow with viral screening and viral load determination representing major areas of active market expansion. Given the commercial value of this technology, great efforts have been invested in research and development of improved amplification procedures (see *Genetic Engineering News* 17:6 (1997)).

Recently developed techniques for amplifying analyte polynucleotides have provided useful alternatives to methods based on the original Polymerase Chain Reaction (PCR) protocol. According to one technique, DNA amplification reactions are performed on solid-phase substrates made alternatively of glass, plastic, a semiconductor chip or a fiber-optic array. Labeled target DNA is synthesized as a molecular bridge between pairs of oligonucleotide primers immobilized to the solid substrate such that the amplification products remain attached to the solid substrate. U.S. Pat. No. 5,399,491 discloses a different technique wherein a target polynucleotide is amplified autocatalytically under conditions of substantially constant temperature, ionic strength and pH. This method, termed Transcription Mediated Amplification (TMA), allows for the synthesis of multiple RNA copies of target sequence. New methods likely to emerge in the future will continue to expand the range of applications that can be addressed by polynucleotide amplification techniques.

Quantitative amplification assays represent one subset of assays that impose stringent requirements on all aspects of the procedure, including template isolation and standardizing amplification efficiency. Approaches that employ internal standards that participate in amplification reactions are intended to normalize reaction efficiency, but fail to account for variable levels of analyte polynucleotide input into the reaction. Related methods that simultaneously amplify an analyte polynucleotide and control polynucleotides derived from constitutively expressed housekeeping genes also are imperfect because multiple primer sets are required to carry out the amplification reaction.

One example of methods based on the use of internal standards in quantitative PCR amplifications is disclosed in U.S. Pat. No. 5,219,727. According to the method disclosed in this patent, the internal standard is included in the amplification reaction and is designed so that it will amplify at a similar efficiency as the target polynucleotide. Like methods that co-amplify constitutively expressed gene products for use as internal standards, the method disclosed in U.S. Pat. No. 5,219,727 requires detecting and quantifying the amplicon derived from the internal standard in order to quantify the analyte polynucleotide. Thus, several steps still are required to quantitate analyte polynucleotides when an internal standard must be detected and quantitated.

The fact that amplified polynucleotides ("amplicons") in conventional PCR and TMA procedures are synthesized as molecules free in solution represents another source of inaccuracy for analyte detection. These amplicons can easily be transferred between samples to produce false-positive results in the contaminated reactions. Standard precautions for minimizing false-positive results due to contamination by carried-over DNA templates include ultraviolet irradiation of pipetting devices, the use of disposable glass- and plastic-ware, use of separate laboratories or laboratory areas for conducting amplification reactions, and avoiding the formation of aerosols. One elaborate approach for ensuring that PCR products cannot be re-amplified in subsequent reactions involves a series of steps using specialized reagents to degrade the products from previous PCR amplifications. However, this procedure is somewhat complicated and involves first substituting dUTP for dTTP in the PCR mixture and then pre-treating all subsequent PCR mixtures with a uracil N-glycosylase (UNG) enzyme prior to PCR amplification. Products from previous PCR amplifications are then eliminated by excising uracil residues using UNG, and degrading the resulting abasic polynucleotide (Longo, et al., *Gene* 93:125 (1990)). Clearly, these methods do not lend themselves to high throughput assays.

Accordingly, there exists a continuing need for techniques that can be used to enhance the precision of polynucleotide amplification procedures. Further, there exists a need for techniques that can be used to diminish the incidence of false-positive results arising from positive carry-over contamination. The present invention addresses both of these needs.

SUMMARY OF THE INVENTION

A first aspect of the invention relates to a method for quantifying analyte polynucleotides that are present in a test sample. The method includes steps for: (1) obtaining a test sample that contains an unknown amount of an analyte polynucleotide; (2) combining a predetermined amount of this test sample with a predetermined amount of a pseudo target; (3) co-amplifying in a polynucleotide amplification reaction the analyte polynucleotide and the pseudo target to produce a collection of amplification products that includes both an analyte amplicon if the sample contained the analyte polynucleotide and a pseudo target amplicon; and (4) quantifying the analyte amplicon without relying on information regarding the amount of pseudo target amplicon produced in the reaction, whereby the quantity of analyte amplicon is related in a dose-dependent manner to the unknown amount analyte polynucleotide that was present in the original test sample. Optionally there can be an added step for detecting the pseudo target amplicon. This optional step may be useful, for example, as a positive control for the amplification reaction. In certain preferred embodiments of the invention, the step for quantifying the analyte amplicon involves first hybridizing the collection of amplification products from the co-amplifying step with a labeled probe that is specific for the analyte amplicon but not the pseudo target amplicon, and then detecting any labeled probe that specifically hybridized to the analyte amplicon. Of course, it is to be understood that the analyte amplicon-specific probe can be a probe that binds the analyte polynucleotide or a nucleic acid strand that is complementary thereto. In other embodiments, the polynucleotide amplification reaction in the co-amplifying step can be any one of a Transcription Mediated Amplification (TMA) reaction, a NASBA reaction or a Polymerase Chain Reaction, with the TMA reaction representing a highly preferred embodiment of the invention. Regardless of the type of amplification reaction that is employed, the obtaining step can involve first collecting a biological specimen and then releasing nucleic acids contained in the specimen to result in the sample that contains the unknown amount of analyte polynucleotide. For all types of amplification reactions the amount of pseudo target in the combining step preferably is between $1\times10^3$ and $2\times10^8$ molecules, more preferably between $1\times10^4$ and $2\times10^8$ molecules, and still more preferably between $1\times10^5$ and $2\times10^8$ molecules. Optionally there can be included an additional step for capturing the analyte polynucleotide onto a solid support prior to the co-amplifying step. In embodiments of the invented method that employ the additional capturing step the amount of pseudo target used in the combining step preferably ranges from between $1\times10^3$ and $2\times10^8$ molecules, more preferably between $1\times10^4$ and $2\times10^8$ molecules, and still more preferably between $1\times10^5$ and $2\times10^8$ molecules. An exemplary solid support is a bead that is derivatized with a synthetic polynucleotide. The biological specimen used in the procedure can be a blood sample or a plasma sample, and the nucleic acids contained in the specimen can include viral nucleic acids. In one embodiment of the invention, the analyte polynucleotide used in the procedure is a nucleic acid that is released from HIV virions. When the polynucleotide amplification reaction used in the invented method is the TMA reaction, there can be included in the method a further step for isolating the analyte polynucleotide and the pseudo target after the combining step and before the co-amplifying step. In embodiments of the invented method wherein the Transcription Mediated Amplification reaction is employed, the amount of the pseudo target used in the reaction preferably is between $1\times10^3$ and $2\times10^8$ molecules, more preferably between $1\times10^4$ and $2\times10^8$ molecules, and still more preferably between $1\times10^5$ and $2\times10^8$ molecules. When the step for quantitatively detecting involves hybridizing a labeled probe that is specific for the analyte amplicon, the labeled probe can be labeled with acridinium ester, in which case the step for quantitatively detecting may involve performing luminometry. In embodiments of the invention wherein the obtaining step involves collecting a biological specimen and releasing nucleic acids contained therein, the analyte polynucleotide can be a viral polynucleotide. In general, the invented method can involve the further step of consulting a standard curve that relates pre-amplification amounts of analyte polynucleotide and post-amplification amounts of analyte amplicon. This step for consulting a standard curve also is applicable when luminometry is employed to measure hybridization of probes labeled with acridinium ester, or when the amplification reaction is particularly a Transcription Mediated Amplification reaction. In still other preferred embodiments that employ the Transcription Mediated Amplification reaction, a paired set of oligonucleotide primers having the sequences of SEQ ID NO:1 and SEQ ID NO:2 can be used for conducting the reaction, and the pseudo target can have a polynucleotide sequence selected from the group consisting of SEQ ID NO:4 and SEQ ID NO:9.

Another aspect of the invention concerns a method for relating pre-amplification amounts of analyte polynucleotide and post-amplification amounts of analyte amplicon. This method includes steps for: (1) obtaining a plurality of control samples that include different predetermined amounts of an analyte polynucleotide; (2) combining each of the plurality of samples with a constant amount of a pseudo target to result in a plurality of mixed samples; (3) co-amplifying in a plurality of amplification reactions both the pseudo target and any of the analyte polynucleotide present in each of the plurality of mixed samples to produce amplification products, the amplification products including both a pseudo target amplicon for each of the plurality of mixed samples and an analyte amplicon for any of the plurality of mixed samples that contained the analyte polynucleotide; (4) quantifying the analyte amplicon for each of the plurality of amplification reactions without reference to the amount of pseudo target amplicon present in the collection of amplification products; and (5) preparing a standard curve having the different predetermined amounts of analyte polynucleotide plotted against the quantified amounts of analyte amplicon for each of the plurality of amplification reactions, thereby relating the pre-amplification amounts of analyte polynucleotide present in each of the plurality of control samples and the post-amplification amounts of analyte amplicon synthesized in each of the amplification reactions. Optionally there can be an added step for detecting the pseudo target amplicon. This optional step may be useful, for example, as a positive control for the amplification reaction. In a preferred embodiment the analyte polynucleotide is a viral polynucleotide, such as an HIV polynucleotide. Generally, the constant predetermined amount of pseudo target can range between $1\times10^3$ and $2\times10^8$ molecules, more preferably between $1\times10^4$ and $2\times10^8$ molecules, and still more preferably between $1\times10^5$ and $2\times10^8$ molecules. According to other embodiments of the invented method, the plurality of amplification reactions in the co-amplifying step can be any of a plurality of Transcription Mediated Amplification reactions, a plurality of NASBA reactions and a plurality of PCR reactions. In a collection of highly preferred embodiments, the amplification reactions in the co-amplifying step are Transcription Mediated Amplification reactions. Regardless of the type of amplification reactions that are employed, the quantifying step can involve first hybridizing the amplification products from the co-amplifying step with a labeled probe specific for the analyte amplicon but not the pseudo target amplicon and then quantitatively detecting any labeled probe that specifically hybridized. In certain instances, the labeled probe is labeled with acridinium ester. In still other preferred embodiments wherein the quantifying step involves hybridization with a labeled analyte amplicon-specific probe, there can be an additional step for capturing the analyte polynucleotide onto a solid support prior to the co-amplifying step.

Yet another aspect of the invention relates to kits that can be used for performing polynucleotide amplification reactions using analyte polynucleotide templates. Exemplary kits can include: a pseudo target; at least one pair of oligonucleotide primers for co-amplifying the pseudo target and the analyte polynucleotide; reagents for carrying out the polynucleotide amplification reaction, including deoxynucleotide triphosphates and a DNA polymerizing enzyme; and printed instructions with directions for first carrying out the amplification reaction and then detecting only analyte amplicons produced in the amplification reaction. In one embodiment, the invented kit can also include a labeled probe for detecting any analyte amplicons produced in the amplification reaction. According to another embodiment, the invented kit further includes nucleotide triphosphates and an RNA polymerizing enzyme. The DNA polymerizing enzyme included in the kits can be a reverse transcriptase. In a highly preferred embodiment, no RNase H additional to that provided by the reverse transcriptase is used in the kit.

Yet another aspect of the invention relates to a qualitative method of determining whether a biological sample contains an analyte polynucleotide. This method includes steps for: (1) obtaining a biological sample to be tested for the presence of the analyte polynucleotide; (2) combining the biological sample with a pseudo target to result in a mixed sample; (3) isolating nucleic acids from the mixed sample, whereby there is obtained a collection of molecules that include the pseudo target and any of the analyte polynucleotide present in the biological sample; (4) conducting a polynucleotide amplification reaction to co-amplify the pseudo target and any of the analyte polynucleotide contained in the collection of molecules to produce amplification products, whereby pseudo target amplicons are formed, and whereby analyte amplicons are formed if the collection of molecules included the analyte polynucleotide; (5) detecting in the amplification products any of the analyte amplicons without detecting the pseudo target amplicons; and (6) determining that the biological sample contains the analyte polynucleotide if the analyte amplicons are detected among the amplification products. In certain embodiments, the amplification reaction is any of a Transcription Mediated Amplification reaction, a NASBA reaction and a PCR reaction. In certain highly preferred embodiments, the amplification reaction is a Transcription Mediated Amplification reaction. When the Transcription Mediated Amplification reaction is employed, the obtaining step can involve drawing blood. Regardless of the type of amplification reaction that is employed, the detecting step can involve first hybridizing a labeled polynucleotide probe having binding specificity for the analyte amplicons and then measuring the extent of specific binding of the labeled polynucleotide probe. When the detecting step involves hybridizing a labeled analyte amplicon-specific probe, the isolating step can involve immobilizing the pseudo target and the analyte polynucleotide to a solid support. According to another preferred embodiment, the detecting step involves detecting by luminometry. In still yet another preferred embodiment, the analyte polynucleotide is from HIV virions. When this is the case, the pseudo target can have a sequence that is either SEQ ID NO:4 or SEQ ID NO:9.

DEFINITIONS

As used herein, the following terms have the following meanings unless expressly stated to the contrary.

A "polynucleotide" may be either RNA or DNA unless specified otherwise.

An "oligonucleotide" is a polynucleotide molecule having a length of from 10 to 100 nucleotides, or more preferably 10 to 50 nucleotides. Ordinarily, oligonucleotides will be synthesized by organic chemical methods and will be single-stranded unless specified otherwise. Oligonucleotides may be labeled with a detectable label.

An "amplicon" is a polynucleotide product generated in an amplification reaction.

An "analyte amplicon" is a polynucleotide product of an amplification reaction wherein an analyte polynucleotide served as the template for synthesis of polynucleotide copies or amplification products.

An "analyte polynucleotide" is a target polynucleotide that is to be replicated by a nucleic acid amplification process such as the TMA protocol, but is structurally distinguishable from a pseudo target polynucleotide. The two polynucleotides may be distinguishable, for example, by virtue of the presence or absence of a restriction enzyme cleavage site or an internal sequence difference that is distinguishable by a hybridization probe.

A "target polynucleotide" has a target sequence to be replicated, may be either single-stranded or double-stranded, and may include sequences in addition to the target sequence, which additional sequences may not be amplified.

A "target sequence" refers to the particular nucleotide sequence of the target polynucleotide which is to be amplified. The target sequence includes the complexing sequences to which oligonucleotide primers useful in the amplification reaction can hybridize prior to extension by a DNA polymerase. Where the target polynucleotide is originally single stranded, the term "target sequence" will also refer to the sequence complementary to the target polynucleotide. Where the target polynucleotide is originally double-stranded, the term "target sequence" refers to both the (+) and (−) strands that are complementary to each other.

A "pseudo target" is a polynucleotide that can be co-amplified with the analyte polynucleotide in a single amplification reaction. The pseudo target and the analyte polynucleotide may be amplified using the same set of oligonucleotide primers. However, it is also possible for the pseudo target and the analyte polynucleotide to co-amplify using independent primer sets. The pseudo target and the analyte polynucleotide will be nonidentical molecules so that the analyte polynucleotide and the pseudo target can be distinguished from each other.

A "pseudo target amplicon" is a polynucleotide product of an amplification reaction wherein a pseudo target served as the template for synthesis of polynucleotide copies or amplification products.

A "polynucleotide amplification reaction" is a template-dependent in vitro enzyme-catalyzed reaction for increasing the number of target polynucleotides.

In the context of the invention, "quantitatively detecting" or "quantifying" refers to a process for determining the extent of polynucleotide or amplicon production.

A "labeled probe" is a nucleotide polymer that harbors a detectable moiety and that can combine with a complementary single-stranded target nucleic acid sequence to form a double-stranded hybrid. The term also includes analogs of naturally occurring nucleotides and particularly includes analogs having a methoxy group at the 2' position of the ribose (OMe). The detectable moiety may be attached to the end(s) of the probe or may be positioned internally within the sequence of the probe. In general, labeled probes will be about 10 to about 100 nucleotides in length, but can be longer than 100 or shorter than 10 nucleotides, A "detectable moiety" is a molecule attached to, or synthesized as part of, a labeled probe. This molecule should be uniquely detectable and will allow the probe to be detected as a result. These detectable moieties are often radioisotopes, chemiluminescent molecules, enzymes, haptens, or even unique oligonucleotide sequences.

A "labeled probe specific for an analyte amplicon" is a labeled probe having a polynucleotide sequence complementary to a polynucleotide product synthesized in an amplification reaction wherein an analyte polynucleotide served as the template for synthesis of amplification products. Since an amplicon is a polynucleotide product generated in an amplification reaction, the labeled probe specific for the analyte amplicon can be complementary to any polynucleotide strand generated in the reaction. Thus, if an analyte polynucleotide is a single-stranded molecule that contains a target sequence, and if copies of the target sequence and its complement are generated in the amplification reaction, then the labeled probe specific for the analyte amplicon can be complementary to the target sequence or its complement.

"Co-amplifying" as used herein refers to the process of amplifying in a polynucleotide amplification reaction more than one species of target polynucleotide. For example, "co-amplifying an analyte polynucleotide and a pseudo target" is intended to refer to the process of simultaneously amplifying the two polynucleotides to result in the formation of analyte amplicons and pseudo target amplicons, respectively.

As used herein "obtaining" a sample that includes, or that may include, an analyte polynucleotide can mean either obtaining from a biological subject such as a human, or obtaining from a reagent depository, such as a commercial vendor. When a sample is obtained from an animal or a human it will be understood that any number of appropriate means familiar to those having ordinary skill in the art can be employed. For example, if a blood sample is obtained, it can be obtained either by drawing blood through venepuncture, but also can be obtained as a forensic sample.

As used herein, the phrase "without reference to the amount of pseudo target amplicon" means that quantitative information regarding the amount of pseudo target amplicon synthesized in an amplification reaction is not required to make a determination regarding another parameter in an amplification system. For example, the synthesized amount of analyte amplicon in an amplification system or the amount of analyte polynucleotide that would have led to the formation of that amount of amplicon can be determined according to the methods disclosed herein without quantitative information about the formation of pseudo target amplicons in the same reaction. Indeed, it is not even necessary to detect the pseudo target amplicon for success of the quantitative method described herein. The present invention provides an approach for relating the pre-amplification amount of analyte polynucleotide and the post-amplification amount of analyte amplicon. This relationship can be established without relying on, or even having knowledge about, the amount of pseudo target amplicon that is co-amplified with the analyte amplicon in an amplification reaction. Thus, even if the pseudo target amplicon is detected or quantified in an experimental procedure, it is unnecessary to employ that information when relating the pre-amplification amount of an analyte polynucleotide and the post-amplification amount of a corresponding analyte amplicon.

As used herein, a "standard curve" is a representation that relates a pre-amplification amount of a polynucleotide and a post-amplification amount of a corresponding amplicon. For example, a standard curve can be a graph having known numbers of input template molecules on the x-axis, and either RLU values or pmols of amplicon product plotted on the y-axis. Standard curves typically are produced using control polynucleotide standards having known numbers of polynucleotide templates. Standard curves can be stored in electronic form or can be represented graphically.

A "biological specimen" is a sample of material derived from an organism.

BRIEF DESCRIPTION OF THE DRAWINGS

FIG. 3*a* shows how low or high starting levels of analyte polynucleotide (TA) serve as templates for conversion of reactants (R) into similar amounts of analyte-specific products (SP). FIG. 3*b* shows that including pseudo targets (PsT) in amplification reactions having low or high starting levels of analyte polynucleotide results in quantitative relationships between the levels of analyte-specific products synthesized in the reactions and the input levels of templates. The diagram shows that pseudo targets serve as templates in the reaction for the synthesis of pseudo target-specific products (PTSP) while analyte polynucleotides serve as templates for the synthesis of analyte-specific products.

FIG. 4*a* shows results be expected for a hypothetical amplification reaction that produces only analyte-specific amplicons. FIG. 4*b* shows results expected for amplification reactions that spontaneously produce low levels of non-specific amplification products that are unrelated to the analyte polynucleotide. FIG. 4*c* shows results expected for amplification reactions that spontaneously produce high levels of non-specific amplification products that are unrelated to the analyte polynucleotide. FIG. 4*d* shows idealized results expected for reactions that include pseudo targets.

FIG. 5 is a schematic diagram illustrating how variability in the efficiency of recovery of a collection of polynucleotides that includes an analyte polynucleotide and a pseudo target can yield similar quantities of amplicon following an amplification reaction. The analyte polynucleotide and the pseudo target are shown at the top of the diagram in a fixed starting ratio. Whether 100% or 50% of the polynucleotide sample is input into the amplification reaction, the final amounts of amplicon products are similar.

DETAILED DESCRIPTION OF THE PREFERRED EMBODIMENTS

Herein I disclose that polynucleotide amplification reactions that included a pseudo target advantageously exhibited improved precision with respect to the amount of analyte amplicon synthesized. Additionally, qualitative amplification reactions can be transformed into quantitative assays by including pseudo targets in the reactions and then quantitatively measuring the amount of analyte amplicon that was synthesized. Also disclosed is a new method of specimen processing which advantageously ensures the production of a pre-established ratio of pseudo target and analyte amplicons in a subsequent amplification reaction, regardless of the efficiency with which nucleic acids were isolated from the specimen. According to this method, pseudo targets are added to a biological specimen before nucleic acids are isolated from the specimen. Assays performed in a qualitative format employing pseudo target amplification, and that provide semi-quantitative information about the amount of analyte polynucleotide in a test sample are also described.

Introduction and Overview

An observation which led to the development of the invention concerned an inherent feature of the standard TMA reaction. More specifically, it was observed that enzymatic synthesis of nonspecific amplification products represented a substantial proportion of the reaction product when the reaction was initiated using only very low amounts of target polynucleotide. When visualized following electrophoresis, the nonspecific amplification products appeared as a smear that extended over a broad size range. This result is illustrated schematically in FIG. 1.

Figure 1:
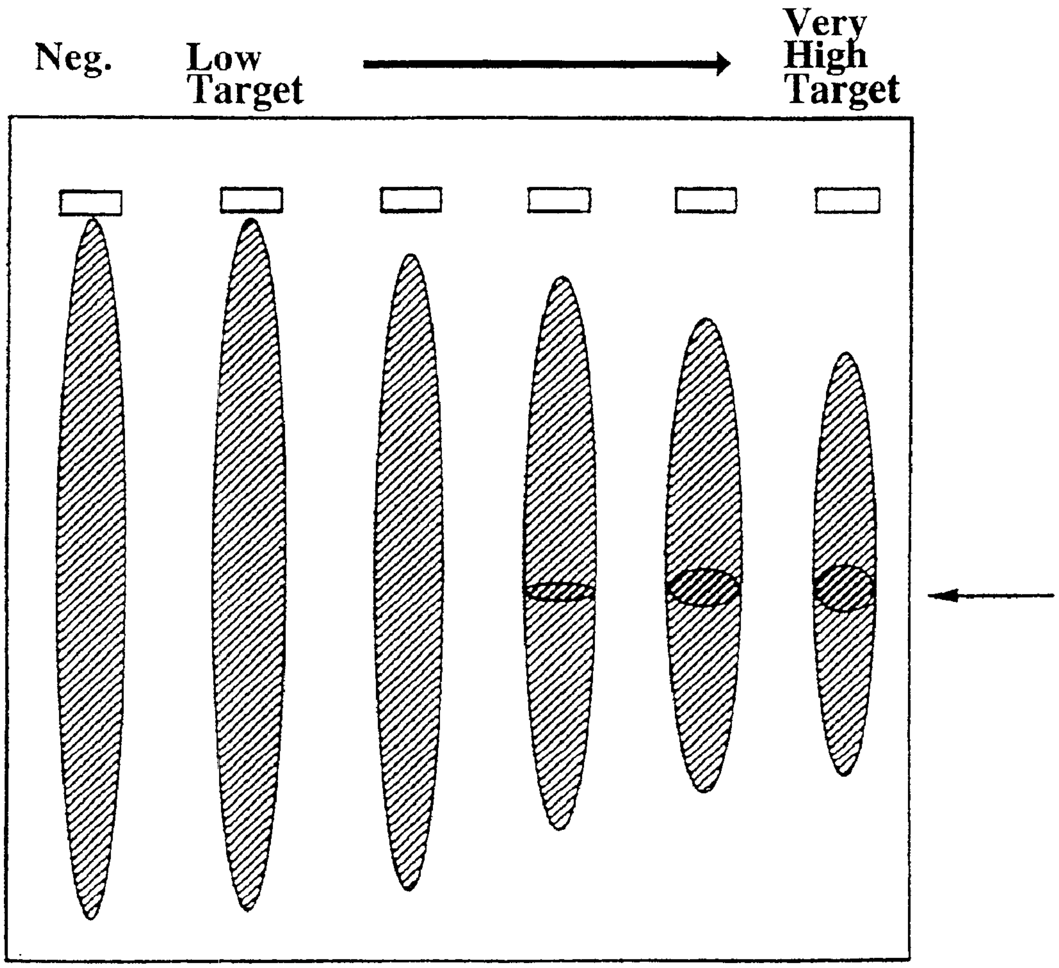
FIG. 1 is a schematic representation of electrophoretically separated TMA reaction products synthesized using different amounts of input target polynucleotide template. The lane marked "Neg" represents a reaction that did not include input template. The remaining lanes represent reactions conducted using increasing amounts of input target polynucleotide. The position on the gel of the specific amplification product derived from the target polynucleotide is marked by an arrow.

Importantly, it was observed that TMA reactions carried out using increasing amounts of target polynucleotide templates resulted in diminished relative contributions of the nonspecific products. This result also is illustrated in FIG. 1. Reactions that were initiated using higher concentrations of target polynucleotides resulted in the formation of larger amounts of specific products and only small amounts of nonspecific products. This inverse relationship led to speculation that nonspecific reaction product formation could be suppressed by including an amplifiable template in the reaction mixture at the time the reaction was initiated.

While not wishing to be bound by any particular theory, this inverse relationship may have been particularly noticeable in autocatalytic reactions such as the TMA reaction because, unless interrupted prematurely, the nature of the reaction is to proceed to an end-point where the supply of available reactants is exhausted and no further synthesis can take place. A TMA reaction that proceeds indefinitely in the absence of a target polynucleotide will generate nonspecific products until the reactants are depleted and no additional synthesis occurs. A PCR reaction carried out indefinitely is also expected to proceed to a point where the reactants are exhausted and amplicon production ceases, and can also generate nonspecific amplification products (for example, see D. Persing in *Diagnostic Molecular Microbiology*; Ch 3, p. 58 (1993)).

As the method disclosed herein is ordinarily practiced, detection of the analyte amplicon is used to indicate the presence of analyte polynucleotides in a population of nucleic acid molecules. For example, a procedure for monitoring the serum level of human immunodeficiency virus (HIV) virions could involve amplifying a portion of the HIV genome and then detecting and quantitating that amplification product. If the procedure further included amplifying a pseudo target, then detection of the pseudo target amplicon would be an optional step that would not be required for success of the assay. Detection of the pseudo target amplicon could be used as a positive control procedure for indicating that an amplification reaction had occurred (i.e., an internal amplification control). However, quantitative characterization of the amount of analyte amplicon synthesized in an amplification reaction, or the quantity of analyte polynucleotide template that would have led to the formation of that amount of analyte amplicon, does not depend on knowledge of the amount of pseudo target amplicon synthesized in the amplification reaction. Thus, analyte amplicon can be quantified according to the methods disclosed herein without reference to the amount of pseudo target amplicon synthesized in an amplification reaction. A critical feature of the method disclosed herein is that the analyte amplicon must be distinguishable from the pseudo target amplicon. More specifically, it must be possible to detect analyte amplicon without also detecting pseudo target amplicon. In a preferred embodiment the analyte amplicon and the pseudo target amplicon differentially bind at least one hybridization probe so that the two amplicon species can be detected independently.

One point particularly relevant to clinical procedures that employ amplification protocols relates to the variability of recovering polynucleotide templates from different biological specimens. For example, it is common to experience variability in the number of molecules of a given polynucleotide recovered from different tissue samples as the result of variable sample sizes and the complexity of different sample handling procedures. Nucleic acids can bind nonspecifically to glass, plastic and chromatography media such as cross-linked polyacrylamides and dextrans, thereby reducing the efficiency of sample recovery during extensive processing. Additionally, RNA recovered from a biological specimen may have degraded by a variable degree as the result of chemical or enzymatic hydrolysis. Enzymatic hydrolysis is particularly evident in biological samples which contain high concentrations of ribonuclease.

Quantitative Polynucleotide Amplification Assays

Incorporating a pseudo target into a polynucleotide amplification reaction not only can reduce amplification variability from sample to sample, but also can transform even a fully optimized qualitative assay into a quantitative assay. In the case of a polynucleotide amplification system where only specific amplification products are synthesized (meaning that target nonspecific products are not made) the amount of end product amplified from an initial target polynucleotide would be constant regardless of the starting amount of target polynucleotide included in the reaction. This is true when autocatalytic amplification reactions, such as the TMA reaction, proceed to the point where one of the reactants is depleted sufficiently so that the reaction terminates. The total amount of end product synthesized in this situation is largely determined by the initial concentrations of reactants included in the reaction. Such an optimized polynucleotide amplification system is qualitative but not quantitative when the reaction is carried out to the point where the concentration of one of the reactants becomes limiting. This is because the amount of end product produced in the reaction depends on the starting reactant concentrations and not on the starting amount of polynucleotide target.

When a pseudo target is included in an amplification reaction, such as a TMA reaction, the pseudo target preferably will be present at a higher copy number relative to the target polynucleotide. The amplification reaction stops when the amount of product amplified from the target polynucleotide and the pseudo target is sufficiently great that one of the reactants has been depleted. Since the pseudo target ordinarily will represent the dominant amplification species, the extent of amplification of the target polynucleotide is determined by the starting amount of the pseudo target and not by the starting amount of the target polynucleotide. Therefore, by controlling the amount of pseudo target in the amplification reaction, the extent of target polynucleotide amplification can be controlled regardless of the starting amount of target polynucleotide in the reaction. While the combined amount of amplification products will be constant when the reactant concentrations are held fixed, the amount of analyte amplicon produced in the reaction will substantially reflect the starting proportion of the analyte polynucleotide relative to the starting level of pseudo target. In this way, a polynucleotide amplification assay can be made into a quantitative assay because the target polynucleotide will amplify by a pre-determined extent. This is illustrated schematically in FIGS. 2–4.

In general, the methods for converting qualitative polynucleotide amplification reactions into quantitative reactions by including a pseudo target polynucleotide in the reactions are applicable to all known polynucleotide amplification systems, including PCR, NASBA (nucleic acid sequence-based amplification), SDA (strand displacement amplification), and amplification methods using self-replicating polynucleotide molecules and replication enzymes like MDV-1 RNA and Q-beta enzyme. Methods for carrying out these various amplification techniques respectively can be found in U.S. Pat. No. 4,965,188; published European patent application EP 0 525 882, U.S. Pat. Nos. 5,455,166, 5,472,840 and Lizardi et al., *BioTechnology* 6:1197 (1988).

Quantitative Aspects of Amplification Reactions that Include Pseudo Targets

It is appreciated in the field of nucleic acid testing that polynucleotide amplification is an exponential process and that small differences in any of the variables that affect the reaction rate can lead to dramatic differences in the yield of analyte-specific amplicons. Disclosed herein is the novel finding that non-specific amplification products generated in amplification reactions can significantly contribute to total amplicon production and can consume reactants that otherwise would be used to synthesize analyte-specific amplification products. The contribution of non-specific products to the pool of amplification products is significant enough that small changes in the amounts of non-specific amplification products can profoundly influence the magnitude of analyte amplicon production. Thus, it was discovered during the development of the present invention that reducing the amount of non-specific products formed in an amplification reaction advantageously improved the precision of analyte amplicon production and transformed qualitative amplification assays into quantitative assays.

The preferred approach for reducing formation of non-specific products requires including a pseudo target in the amplification reaction and then quantitatively detecting analyte amplicons that are synthesized in the reaction. In this way, analyte amplicon production can be related in a dose-dependent fashion to the amount of analyte polynucleotide present at the time the amplification reaction was initiated. Additionally, in accordance with the invented methods it is unnecessary to detect pseudo target amplicons in order to quantify the number of analyte polynucleotides present in a test sample.

Thus, herein there is disclosed a method of quantifying analyte polynucleotides that does not rely on the detection of amplification products arising from any internal standard. The development of this approach was made possible by recognizing the source of the problem which underlies variability in analyte amplicon production, and which can be controlled by including a pseudo target in the amplification reaction. Although the pseudo target serves as a template in the amplification reaction, detection of pseudo target amplicons is unnecessary for quantifying analyte polynucleotides. While it may seem counterintuitive that precision of an amplification reaction would be improved by adding into the reaction a template that competes with the analyte polynucleotide for reagents needed to synthesize amplicons, the results presented below clearly demonstrate the value of this procedure. Simply stated, the methods disclosed herein represent a procedure for controlling the otherwise highly variable production of non-specific amplification products by introducing into the system template polynucleotides that are amplified, but that are not necessarily detected or quantified.

Figure 3A:
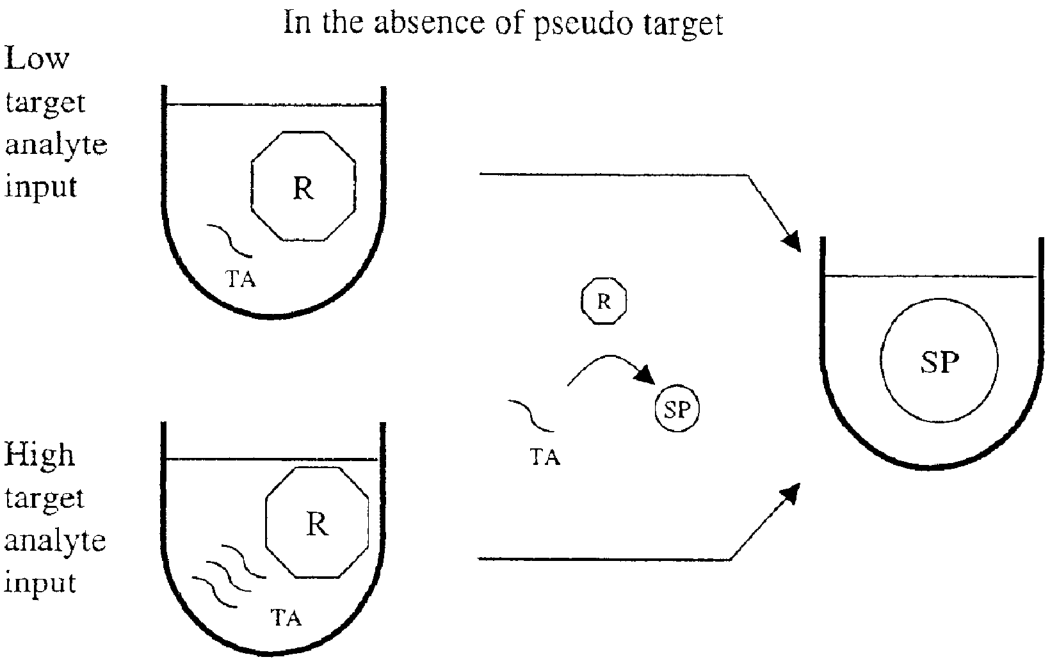
FIGS. 3*a*–3*b* are schematic illustrations showing how inclusion of pseudo targets in idealized reactions that do not produce nonspecific amplification products can transform qualitative assays into quantitative assays.
Figure 3B:
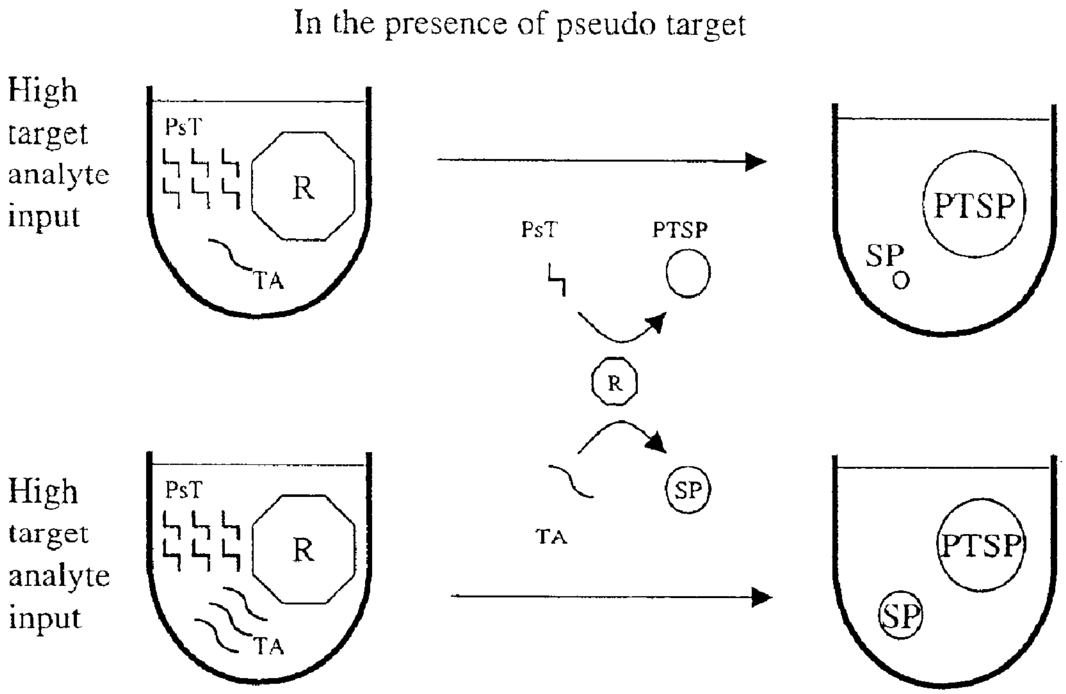

Basis of Improved Precision and Quantitative Capacity of Amplification Reactions FIGS. 3*a*–3*b* illustrate how pseudo targets can transform a qualitative polynucleotide amplification reaction into a quantitative assay. FIG. 3*a* shows how an optimized reaction converts a pool of reactants (represented in the diagram by an octagon) into specific amplification products (SP) using target analyte (TA) polynucleotides as templates. In the absence of a pseudo target the assay is qualitative because the amount of analyte amplicon produced in the reaction is not quantitatively related to the starting level of target analyte polynucleotide. Whether the starting level of analyte polynucleotide is low or high does not alter the amount of analyte amplicon synthesized in the reaction. Instead, the amount of analyte amplicon that can be produced in the reaction is defined by the starting reactant pool and not by the starting level of analyte polynucleotide. Thus, a constant amount of amplicon is produced when the amplification reaction is carried out to the point of reactant depletion. Conversely, FIG. 3*b* shows how amplification reactions conducted in the presence of pseudo targets synthesize analyte-specific products in proportion to the amount of starting analyte polynucleotide when parallel reactions include a pseudo target. More particularly, when polynucleotide amplification reactions include a pseudo target, the final amount of analyte amplicon is related in a dose-dependent fashion to the starting level of analyte polynucleotide that served as a template in the reaction. Accordingly, it is only necessary to quantify the analyte amplicon (and not the pseudo target amplicon) to gain information about the starting level of analyte polynucleotide in the reaction. This method of quantifying polynucleotides advantageously circumvents the need for detecting amplicons other than the analyte amplicon, or for employing different probes to distinguish different amplicon species. Additionally, the same paired set of oligonucleotide primers can be used to amplify both the analyte polynucleotide and the pseudo target, since the two products of the amplification reaction will be distinguishable using an analyte-specific hybridization probe.

Figure 4A:
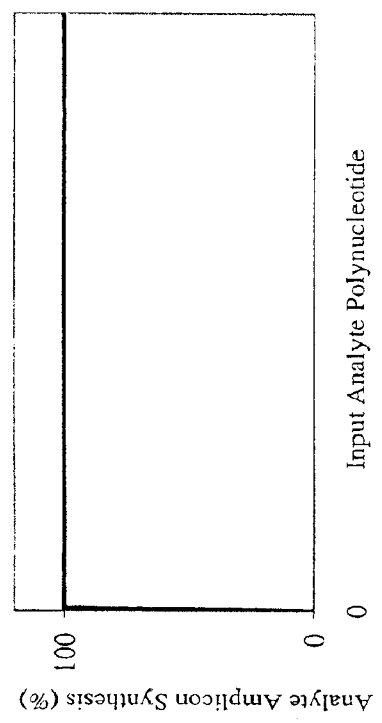
FIGS. 4*a*–4*d* are idealized graphs illustrating how the dynamic range and precision of polynucleotide amplification reactions are improved when the reactions include pseudo targets.
Figure 4B:
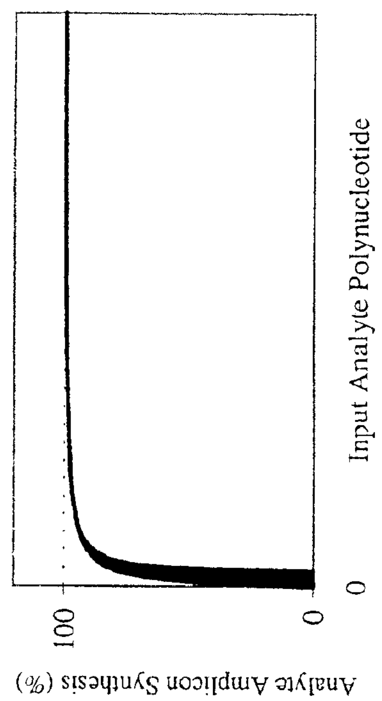
Figure 4C:
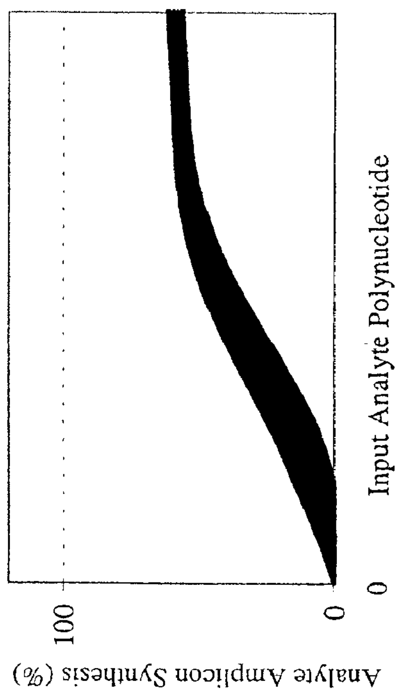

FIGS. 4*a*–4*d* illustrate how analyte amplicon synthesis quantitatively reflects the starting analyte polynucleotide level over an extended range when two competing amplification reactions occur simultaneously. FIG. 4*a* shows results that would be expected for an idealized amplification reaction that takes place in the absence of non-specific product formation. A constant level of analyte amplicon formation is expected at all levels of input analyte polynucleotide. This case reflects the reaction illustrated in FIG. 3*a*. FIG. 4*b* shows results that would be expected for amplification reactions that spontaneously generate non-specific products at low levels. A narrow range of dose-dependency exists only at very low levels of input analyte polynucleotide. FIG.

Figure 4D:
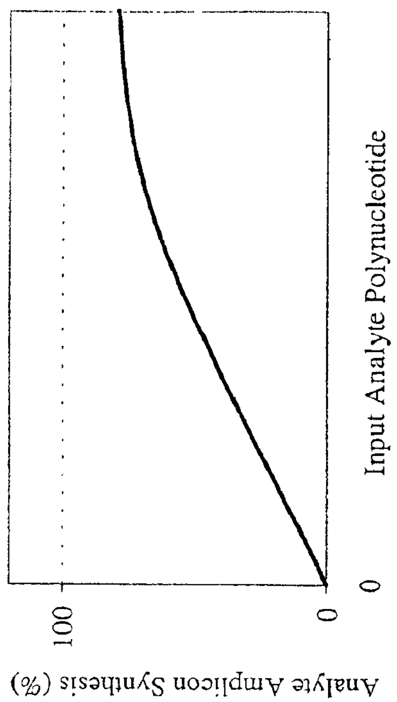

4*c* shows results that would be expected for amplification reactions that spontaneously generate high levels of non-specific amplification products. In this instance, amplification reactions conducted at any given level of input analyte polynucleotide produce amounts of amplicon falling within a range, as indicated on the Y-axis of the graph. The more significant contribution of the non-specific product formation distinguishes the results shown in FIGS. 4*b* and 4*c*. The breadth of the lines relating the input levels of analyte polynucleotide and analyte amplicon synthesis reflects the low precision of analyte amplicon formation and is attributable to the fact that spontaneous formation of non-specific amplification products can be highly variable. FIG. 4*d* shows results that would be expected for an idealized amplification reaction that includes a pseudo target. The amount of analyte amplicon produced in the reaction exhibits both improved precision and a dose-dependent relationship over a broad range of input analyte polynucleotide levels. This case reflects the idealized reaction illustrated in FIG. 3*b*.

Thus, the precision and quantitative aspects of amplification reactions conducted according to the invented method are interrelated by the existence and controllability of competing reactions wherein analyte and non-analyte polynucleotides co-amplify and compete for reactants. Improved dynamic range results when a second amplification reaction competes with the analyte-specific reaction for reactants. Improved precision in the amount of analyte amplicon synthesis results when the second reaction is made highly controllable by including pseudo targets in the amplification reaction at a level of from $1\times10^{3-2\times108}$ molecules per reaction, where a typical reaction has a volume of 100 $\mu$l.

Use of a Standard Curve—Quantifying Pre-Amplification Amounts of Analyte Polynucleotide Since amplification reactions that include pseudo targets advantageously feature quantitative relationships between the number of analyte polynucleotides input into the reaction and the number of analyte amplicons synthesized, the number of analyte polynucleotides present in a test sample can be determined using a standard curve. More particularly, a plurality of amplification reactions containing constant amounts of pseudo target and known amounts of analyte polynucleotide standard can be run in parallel with an amplification reaction prepared using a test sample containing an unknown number of analyte polynucleotides. Alternatively, a standard curve can be prepared in advance so that it is unnecessary to prepare a curve each time an analytical procedure is carried out. Such a curve prepared in advance can even be stored electronically in a memory device of a testing instrument. Preferred amplification methods include Transcription Mediated Amplification reactions, NASBA reactions and Polymerase Chain Reactions. Transcription Mediated Amplification is highly preferred. The amounts of pseudo target used should be the same for each reaction and preferably fall in the range of from $10^3$ to $2\times10^8$, from $10^4$ to $2\times10^8$, from $10^5$ to $2\times10^8$, or from $10^7$ and $2\times10^8$ pseudo target molecules per reaction. Reactions that include pseudo targets can be carried out according the methods described herein with the number of analyte amplicons synthesized in each reaction being quantified by standard hybridization and detection procedures. Although detection of pseudo target amplicons is unnecessary for quantifying pre-amplification amounts of analyte polynucleotide in the test sample, detection of pseudo target amplicons optionally can be used to confirm success of the amplification reactions. In this way detection of pseudo target amplicons serves as an internal amplification control. A standard curve having pre-amplification amounts of the analyte polynucleotide standard on a first axis and corresponding post-amplification amounts of analyte amplicon on a second axis is then prepared. The post-amplification amount of analyte amplicon measured for the test reaction is then located on the post-amplification axis of the standard curve. The corresponding value on the other axis of the curve represents the pre-amplification amount of analyte polynucleotide that was present in the test reaction. Thus, determining the number of molecules of analyte polynucleotide present in the test sample is accomplished by consulting the standard curve, or more particularly by comparing the quantitative results obtained for the test sample with the standard curve, a procedure that will be familiar to those having an ordinary level of skill in the art.

The procedures described herein can easily be used to quantify analyte polynucleotides present in a test sample. Indeed, if a plurality of pseudo target-containing control amplification reactions are initiated using known numbers of molecules of an analyte polynucleotide standard, and if a test reaction that includes the pseudo target is initiated using an unknown number of analyte polynucleotide molecules, then it becomes possible after quantifying the number of analyte amplicons in each reaction to determine the number of analyte polynucleotide molecules that must have been present in the test sample. For example, if standard reactions that respectively included 500, 1,000 and 1,500 molecules of analyte polynucleotide standard produced analyte amplicon signals of 1×, 2×and 3×following an analyte-specific probe-based hybridization procedure, and if the test sample produced an analyte amplicon signal corresponding to 1.5×, then the test sample must have contained 750 analyte polynucleotide molecules. In this exemplary case a linear relationship exists between the signal generated by the amplicons arising from the analyte polynucleotide standard in the range of from 500 to 1,500 molecules. The relationship between the number of analyte polynucleotide molecules input into the standard amplification reactions and the amplicon-specific signal strength is most conveniently established using a graph. Determining the number of analyte polynucleotide molecules present in a test sample is simply a matter of determining from the standard graph the number of analyte polynucleotide molecules that correspond to a measured analyte amplicon signal strength. This illustrates how analyte polynucleotide standards can be used in connection with pseudo targets in polynucleotide amplification reactions to quantify pre-amplification amounts of analyte polynucleotide contained in test samples.

Structural Features of Useful Pseudo Target Polynucleotides

The following information can be used to design pseudo target polynucleotides for use in connection with the methods disclosed herein. Given this information, useful pseudo targets corresponding to any number of analyte polynucleotides that are to be detected and quantified can be made. Exemplary applications where pseudo targets may be used in connection with polynucleotide amplification procedures include, but are not limited to: (1) detecting a bacterial or viral pathogen; (2) quantitating polynucleotides where such quantitation is useful as an indicator of a disease process, such as HIV disease progression; and (3) numerous other applications including forensic analysis, environmental and food testing.

In one preferred embodiment of the invention the pseudo target and the analyte polynucleotide are amplifiable using the same set of two oligonucleotide primers. In this instance, a single oligonucleotide primer that will have a complementary binding site on the pseudo target also will have a complementary binding site on the analyte polynucleotide.

In another preferred embodiment the pseudo target and analyte polynucleotide, which are to serve as templates in an amplification reaction, amplify with substantially similar efficiencies. Thus, whether the amplification is carried out using TMA, PCR or some other procedure such as SDA (strand displacement amplification) or methods employing self-replicating polynucleotide molecules and replication enzymes like MDV-1 RNA and Q-beta enzymes, the pseudo target and analyte polynucleotides preferably will have similar amplification efficiencies.

One way to ensure that the pseudo target and analyte polynucleotide templates will have similar amplification efficiencies is to require that the two templates exhibit closely related, but nonidentical, polynucleotide sequences over the span of the sequence that is amplified in the procedure. For example, a pseudo target polynucleotide may be created by scrambling an internal portion of the sequence of an analyte polynucleotide, where the scrambled sequence corresponds to the portion of the analyte polynucleotide that serves as the part of the molecule that is hybridized by a probe specific for the analyte polynucleotide. The length of the pseudo target polynucleotide is not critical to its operation in the practice of the methods disclosed herein.

It is essential that the pseudo target and the analyte polynucleotide are co-amplifiable in a single reaction, and that the resulting two amplicon species can be detected independently. More particularly, it is essential that the pseudo target and analyte polynucleotide amplification products have polynucleotide sequences that differ from each other so that the two products can be distinguished by length, by the ability to hybridize to a detection probe, or by other methods. Since the polynucleotide templates amplified in the amplification reactions ordinarily will contain a substantial number of nucleotide bases interposed between the regions homologous or complementary to the primer binding sites used to carry out the amplification reaction, these interposed sequences may serve as regions to which selected hybridization probes can bind. Criteria useful for selecting hybridization and detection probes will be familiar to those having an ordinary level of skill in the art. Probes useful in connection with the invention include labeled polynucleotides as well as oligonucleotides useful as primers in subsequent amplification reactions.

When the pseudo target is added to a biological specimen at a time before analyte polynucleotide is isolated from the specimen, for example as an aid to sample processing, it is important that the pseudo target and the analyte polynucleotide are recoverable from the specimen by the same sample processing procedure. For example, if the analyte polynucleotide is recoverable under strongly alkaline conditions that denature DNA and hydrolyze RNA, then it should also be true that the pseudo target is recoverable as a structurally intact molecule under the same conditions. Thus, if alkaline buffer conditions are used to isolate analyte polynucleotides in the presence of added pseudo target polynucleotides, then neither the analyte nor the pseudo target would be an RNA molecule that would be degraded during the isolation procedure. Similarly, if the pseudo target and the analyte polynucleotide are to be precipitated, for example by the addition of an alcohol such as ethanol, then the pseudo target and the analyte polynucleotide should precipitate with substantially similar efficiencies.

Relationship between Pseudo Target and Analyte Polynucleotide Sequences

Significantly, it is preferred but not essential for the pseudo target and the analyte polynucleotide to be co-amplifiable using the same set of two oligonucleotide primers. More specifically, qualitative polynucleotide amplification assays for detecting an analyte polynucleotide using a paired set of analyte-specific primers can be transformed into quantitative assays by further including in the reaction a pseudo target and a set of primers for amplifying the pseudo target. In one embodiment of the invented method, the analyte polynucleotide and the pseudo target are co-amplifiable using the same two primers.

It is also possible to employ a "universal pseudo target" and a set of pseudo target-specific primers to produce quantitative amplification reactions. In one embodiment of the invention, the primers used for amplifying the universal pseudo target can be the same as the primers used for amplifying the analyte polynucleotide. The universal pseudo target need not be related to the structure of the analyte polynucleotide, and need not co-amplify with the analyte polynucleotide with similar amplification efficiency. Amplification reactions conducted using low or high starting levels of analyte polynucleotide will synthesize analyte amplicons in a fashion that is dose-dependent on the starting amounts of analyte polynucleotide present when the amplification reactions were initiated. Using this procedure, two or more amplification reactions can be assessed for the production of analyte amplicons, with the analyte amplicon levels being related to the starting levels of analyte polynucleotide in each sample in a dose-dependent manner.

While good results can be achieved using pseudo targets and associated primers that are unrelated to the analyte polynucleotide, it is preferable to employ pseudo targets that co-amplify with the analyte polynucleotide using the same set of primers. This preferred approach advantageously reduces variability in the composition of the reagent pool used as a resource for synthesizing amplicons in the amplification reaction. However, the illustrative Examples presented herein for describing the invention employ pseudo targets and exemplary analyte polynucleotides that co-amplify using common sets of oligonucleotide primers.

Choosing an Amount of Pseudo Target to be Included in an Amplification Reaction

In general, the positive benefits achieved by including pseudo targets in polynucleotide amplification reactions are achievable over a very broad range of pseudo target concentrations. More particularly, including pseudo targets in amplification reactions, such as TMA reactions, in amounts ranging from $1\times10^3$–$2\times10^8$molecules will result in: (1) higher precision of amplification, (2) reduced likelihood of positive carryover and (3) normalization of target recovery variability, all as disclosed herein. Within practical limits, higher starting levels of pseudo target in an amplification reaction will result in greater improvement of the three above-referenced parameters.

Since pseudo target amplicons will be synthesized using nucleotide triphosphate reactants that otherwise could be used to synthesize analyte amplicons, the presence of a pseudo target in an amplification reaction will result in a reduction of the synthesis of analyte amplicons. This is because both analyte amplicons and pseudo target amplicons are synthesized from a limited pool of reactants. Accordingly, increasingly high starting levels of pseudo target will result in decreasing amounts of analyte amplicon produced in the amplification reaction. Thus, the upper limit of starting pseudo target concentration in an amplification reaction will be a practical matter dependent on the sensitivity of the procedure used for detecting the analyte amplicon.

The upper limit amount or concentration of a pseudo target that can be included in an amplification reaction, and that will yield levels of analyte amplicon adequate for detection, is most easily determined by routine experimentation. Again, it will be readily apparent to those having ordinary skill in the art that higher levels of pseudo target in an amplification reaction conducted to the point of reagent exhaustion will result in lower amounts of analyte amplicon produced in the reaction. This is because pseudo target amplicons are synthesized at the expense of analyte amplicons in the amplification reaction. Thus, amplification reactions that include very high levels of a pseudo target will result in the production of low levels of analyte amplicon. Highly sensitive assays for detecting analyte amplicons will be particularly useful for detecting these lower levels of analyte amplicon. Conversely, less sensitive assays that require larger amounts of analyte amplicon for a positive detection signal will be useful for detecting larger quantities of analyte amplicon that might result from amplification reactions that included only low starting levels of pseudo target, and that resulted in higher levels of analyte amplicon. Thus, the upper limit of the amount of pseudo target that can be used for conducting an amplification reaction will depend on the sensitivity of the assay that is ultimately to be used for detecting analyte amplicons, and not on the amplification reaction itself.

Since it is generally true that higher levels of input pseudo target provide enhanced reduction of nonspecific amplification products in reactions such as the TMA reaction, it follows that the amount of pseudo target included in an amplification reaction preferably should be as high as possible. The highest pseudo target level disclosed in the Examples which follow was $2\times10^8$ molecules in a 100 $\mu$l reaction. Of course, the detection system used for detecting analyte amplicons must be sensitive enough to give a positive signal when analyte polynucleotides are present in the starting sample so that analyte amplicons are synthesized in the amplification reaction. In practice, a range of pseudo target concentrations can be tested to identify an optimal amount that gives good results in the amplification reaction as measured by detectability of analyte amplicons using a detection system having a given sensitivity for detecting analyte amplicons. Ordinarily, positive and negative controls will be included in this procedure to indicate the results that would be expected for amplification reactions that did or did not include analyte polynucleotides, respectively.

The amount of pseudo target selected for conducting an amplification reaction can be influenced by the magnitude of the amplification, the starting number of analyte polynucleotides in the reaction and on the sensitivity of the detection system used for detecting analyte amplicons. Standard TMA reactions typically amplify starting polynucleotide levels by $10^{12}$–$10^{13}$ fold. An exemplary polynucleotide detection system can detect approximately $6\times10^7$ molecules in a hybridization assay. In order to detect 100 molecules of an analyte polynucleotide in a sample that served as the source of templates in an amplification reaction, it would be necessary to achieve an amplification of approximately $6\times10^5$ fold ($6\times10^7$ divided by 100). To achieve at least $6\times10^5$ fold amplification of the 100 analyte polynucleotide molecules the amplification reaction should not include more than $1\times10^7$ pseudo target molecules. This is because $6\times10^{12}$ (as an example value in the range of from $10^{12}$–$10^{13}$ fold indicated above) divided by $1\times10^7$ equals a $6\times10^5$ fold increase. Including a greater number of pseudo target molecules would reduce the fold amplification to less than the acceptable $6\times10^5$ value. If instead a PCR protocol leading to a $1\times10^9$ fold amplification were employed, the maximum acceptable amount of pseudo target in the amplification reaction would be $1\times10^9$ divided by $6\times10^5$, or $1.7\times10^3$ molecules. Thus, it should be clear that: (1) a broad range of pseudo target concentrations will be useful in the practice of the method disclosed herein, and (2) an optimal amount of pseudo target can be determined empirically when the number of analyte polynucleotides in a sample being tested in an amplification protocol is unknown.

Preferred amounts of pseudo target useful for conducting amplification reactions typically range from between $10^3$ and $10^9$ molecules per reaction, where a typical reaction is conducted in a 100 $\mu$l volume. For example, an assay for detecting HIV polynucleotides in a serum sample isolated from an HIV-infected human can be conducted using between $10^3$ and $2\times10^8$, between $10^4$ and $2\times10^8$ or between $10^5$ and $2\times10^8$, or between $10^7$ and $2\times10^8$ pseudo target molecules per reaction. In a highly preferred embodiment, the amplification reaction is a TMA reaction and the HPA ("homogenous protection assay") method is used for detecting analyte amplicons produced in amplification reactions conducted using these amounts of pseudo target. As indicated in the Examples which follow, broad ranges of pseudo target concentrations have been tested and shown to give good results.

Kits for Performing the Invented Method of Polynucleotide Amplification

Kits useful for performing the polynucleotide amplification methods described herein will include: (1) a pseudo target, (2) oligonucleotide primers for co-amplifying the pseudo target and the analyte polynucleotide, (3) reagents for carrying out the polynucleotide amplification reaction, and (4) printed instructions for carrying out an amplification reaction and for specifically detecting only analyte amplicons produced in the reaction. Optionally the kit may include a labeled probe for detecting analyte amplicons. Reagents included with the kit will comprise deoxyribonucleotide triphosphates and a DNA polymerizing enzyme, which may be a reverse transcriptase. Nucleotide triphosphates and an RNA polymerase are optional reagents that can be included in the kit.

With this background, three particular aspects of the invention now are described in more detail.

I. Enhancing the Precision of Analyte Polynucleotide Amplification

Amplification techniques, both quantitative and qualitative, represent powerful tools for detecting and measuring even trace amounts of specific target polynucleotides. However, difficulty in obtaining uniform amplification efficiency among different reactions means that variability in the extent of amplification compromises the precision of quantitation and the ability to detect small amounts of target. I sought to develop methods that could minimize the formation of nonspecific products, enhance precision in the amount of analyte amplicon synthesis and maximize the ease with which quantitative amplification reactions could be performed.

Figure 2A:
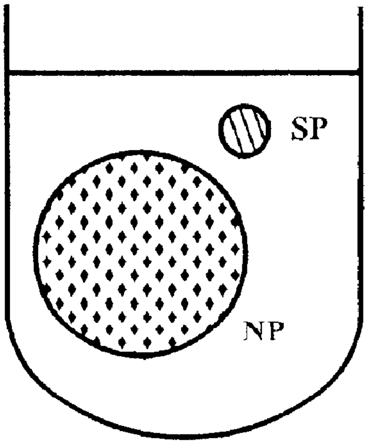
FIGS. 2*a*–2*c* schematically illustrate three different reaction conditions for a TMA reaction. When other variables such as enzyme, primer, and NTP concentrations are held constant, under the condition of low input levels of analyte polynucleotide (FIG. 2*a*) the majority of the reaction product is a template-independent nonspecific product (NP) while the analyte amplicon or specific product (SP) represents only a minor component of the total reaction product. Under conditions of high input levels of analyte polynucleotide (FIG. 2*b*), the analyte amplicon (SP) represents a majority of the total reaction product while the nonspecific product (NP) is a minor component. Under conditions where the level of input analyte polynucleotide is low but the level of pseudo target is high (FIG. 2*c*), pseudo target specific product (PTSP) formation is at the expense of nonspecific product formation.
Figure 2B:
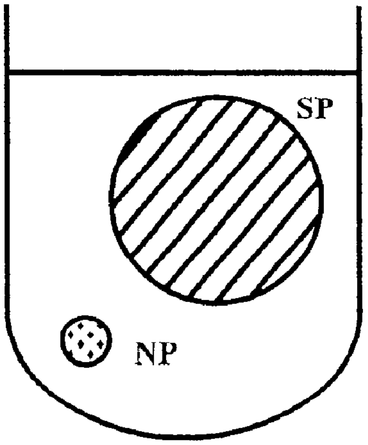
Figure 2C:
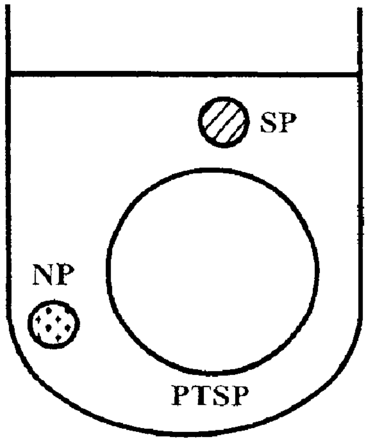

Variability in the extent of amplification appears to be partly attributable to the enzymatic synthesis of nonspecific reaction products. The formation of these nonspecific products was most noticeable when reactions contained only very low starting levels of target polynucleotides that served as amplification templates. At higher levels of target polynucleotide, the formation of nonspecific reaction products was less significant and represented only a small proportion of the total product of the reaction. Thus, an object of the present invention was to simulate reaction conditions that were characteristic of high target polynucleotide concentrations even when starting levels of analyte polynucleotides in the reaction mixtures were very low. More particularly, it was desirable to simulate favorable reaction conditions that would minimize the formation of nonspecific products, as represented in FIG. 2.

Amplification reactions supplemented with pseudo target polynucleotides that co-amplified with the analyte polynucleotide provided the desired reaction conditions to achieve these objectives. This allowed the amplification reaction to behave as if high levels of analyte were present even when the true analyte level in the amplification reaction was low. As indicated by experimental results presented below, adding greater than $10^5$ copies of the pseudo target polynucleotide improved amplification precision as measured by an improved coefficient of variability (CV%) of relative light units (RLUs), where RLUs represent a measurable indicator of the quantity of hybridized probe. In the present context, CV% is a statistical value that is calculated by dividing the standard deviation (SD) for a collection of data by the net average for that collection and then multiplying the result by 100. Lower CV% values reflect less spread among data points and are taken as indicators of higher experimental precision. Thus, the method described herein provides a way to improve the precision with which the analyte polynucleotide is amplified while reducing the formation of variably sized nonspecific reaction products.

The methods disclosed herein additionally provide a mechanism for standardizing the results of polynucleotide amplification reactions regardless of the starting level of analyte polynucleotide as long as the analyte polynucleotide was present at a copy number lower than the copy number of the pseudo target. In an exemplary procedure described below, analyte polynucleotide was present in a set of amplification reaction mixtures at starting levels of from $10^1$–$10^5$ molecules while the pseudo target was present in all mixtures at $10^6$ molecules. This meant that all the amplification reactions were initiated from substantially $10^6$ polynucleotide templates because the contribution of the analyte polynucleotides to the total number of templates in any of the mixtures was minimal. Thus, all of the amplification reactions behaved as though they contained roughly $10^6$ templates even though the number of analyte polynucleotides varied widely. This effectively standardized the amplification reactions to $10^6$ template polynucleotides regardless of actual analyte level.

II. Controlling Amplicon Production

It has been further discovered that pseudo targets can be employed to overcome obstacles associated with the "over production" of analyte amplicons that can lead to inaccurate quantitation of high levels of input target polynucleotide. If excessive amounts of amplicon are produced in an amplification reaction, and if those amplicons are to be quantitated by hybridizing a detection probe to saturation, then large quantities of detection probe necessarily will be consumed in the detection step of the assay. Conversely, if reduced levels of amplicon are produced, then less detection probe will be required to carry out the detection step. Still another advantage of reducing the amount of amplicon produced in an amplification reaction relates to the another aspect of the detection apparatus used for detecting the amplicon. Since detection means such as luminometers often will have linear response ranges that can be saturated at high signal levels, it is an advantage to be able to conduct amplification reactions such that the signal produced in a detection step falls within the linear response range for the detection apparatus. Thus, the ability to control amplicon synthesis clearly is beneficial with respect to subsequent detection steps.

The amount of analyte amplicon generated in the amplification reaction can be controlled by including a pseudo target in the amplification reaction to compete with the target polynucleotide for amplicon synthesis. When the pseudo target is present, reactants in the amplification reaction mixture will be used to synthesize both analyte amplicons and pseudo target amplicons. If the amplification reaction proceeds to reagent exhaustion, and if higher numbers of pseudo target amplicons are produced at the expense of analyte amplicons, then the relative proportion of analyte amplicons can be reduced by increasing the starting amount of pseudo target in the amplification reaction. An appropriate level of pseudo target to be included in the amplification reaction can be determined using no more than routine experimentation.

An alternative approach to reducing analyte amplicon production in a polynucleotide amplification reaction such as the TMA reaction would be to perform the reaction under sub-optimal conditions, such as those described in U.S. Pat. Nos. 5,705,365 and 5,710,029. This alternative may at times be less desirable than the above-described approach because different conditions may be required to "de-optimize" the reaction for different analytes to be detected. In contrast, reducing the amount of analyte amplicon produced in a reaction by including a pseudo target allows all reactions to be performed under optimal conditions.

Thus, including a pseudo target in an amplification reaction provides a means for "tuning" a quantitative amplification reaction by competing high target levels with even higher levels of pseudo target.

III. Specimen Processing in the Presence of Added Pseudo Targets

Uniform recovery of target polynucleotides from different biological samples is very important for many quantitative assays. For example, assays for determining plasma levels of HIV virions easily could lead to an inaccurate estimation of virion levels in the plasma if the precision of target polynucleotide recovery is low. Herein there is described an alternative approach that is relatively tolerant to variability in the level of input analyte polynucleotides.

Rather that striving for quantitative recovery of polynucleotides that will serve as templates in an amplification reaction, one aspect of the invention is directed to a method of normalizing variability of target polynucleotide recovery at the specimen processing step. According to this approach, the final amount of a target polynucleotide amplification product is easily controlled when the level of a pseudo target is sufficiently high that pseudo target amplification competes with true target amplification and when the pseudo target and the analyte polynucleotide are co-amplifiable with similar amplification efficiencies. In this range, the amount of analyte amplicon is inversely proportional to the input level of the pseudo target. For example, if the input level of pseudo target is increased by X fold, then the analyte amplicon will be reduced to 1/X. When pseudo target is present in specimen processing steps, the pseudo target and the true target will be recovered with similar efficiencies. Therefore, if the recovery efficiency for the analyte polynucleotide is K%, then the pseudo target also will be recovered at an efficiency of K%.

Under otherwise identical conditions, reactions will produce a relatively constant amount of amplicon. Thus, addition of pseudo target diverts the reaction components from making nonspecific amplicon and ensures that effectively all of the amplicon produced in the reaction is either pseudo target amplicon or analyte amplicon representing the amplification product of an analyte polynucleotide. The pseudo target amplicon and the analyte amplicon will be produced in the same ratio as the ratio of pseudo target and analyte polynucleotide at the time the amplification reaction was initiated.

When analyte polynucleotides and pseudo targets are co-isolated and then added to an amplification reaction that proceeds to reactant exhaustion, the relative proportion of resulting analyte and pseudo target amplicons will be the same as the relative proportion of analyte and pseudo target polynucleotides in the sample isolated from the biological specimen. This means that, regardless of the efficiency of the polynucleotide recovery in specimen processing, the amount of analyte amplicon synthesized in an amplification reaction will be the same as the amount that would have been synthesized if 100% of the analyte polynucleotide and pseudo target had been recovered in the specimen processing step. Thus, by adding a pseudo target to a biological specimen at the time of processing to isolate polynucleotides for subsequent amplification, the target recovery efficiency will be normalized in the subsequent amplification step.

Amplification Reactions that Include Pseudo Targets

Two convenient formats can be used for performing the TMA reactions that were employed in Examples described below. In the first format, all materials are in a liquid state at all times. For example, solutions of reagents, templates and enzymes are combined in a reaction vessel and the amplification is allowed to proceed. This is most convenient when the target polynucleotide is available in a purified or semi-purified state. In the second format, the polynucleotide template to be amplified in the TMA reaction is first collected on a solid phase (such as a bead), and the complex that includes the solid phase and the template combined with other reagents in the amplification reaction. Useful solid phase supports include but are not limited to nitrocellulose, nylon, glass, coated magnetic particles, polyacrylamide, polystyrene and derivatized polymers such as epoxies. This second format is especially convenient when the template polynucleotide is available in limiting amounts. Those having an ordinary level of skill in the art will appreciate that manipulating small samples of polynucleotides easily can be replaced by manipulating suspensions of the larger and more manageable beads. Moreover, the beads may represent one component in a scheme for purifying the template. For example, beads having an oligo(dT) polynucleotide disposed thereon can be mixed with a cell lysate such that poly(A)$^+$mRNA becomes immobilized on the beads. Thus, the complex that includes the beads and immobilized mRNA can be combined with reagents and enzymes so that a TMA reaction can be performed using the RNA joined to the beads as templates for the amplification. Under this circumstance the beads may be added directly to the reaction vessel. If instead of an oligo(dT) polynucleotide a polynucleotide having a different sequence is immobilized onto beads, that different sequence can be used to capture a complementary analyte polynucleotide or pseudo target from a collection of polynucleotides. This method of immobilizing a particular polynucleotide to a solid support can provide a means for isolating particular polynucleotides from a complex mixture of polynucleotides. Other methods of isolating polynucleotides can involve standard procedures such as extraction with organic reagents such as mixtures of phenol and chloroform, optionally including alcohol precipitation steps.

The following Examples demonstrated that the presence of pseudo targets advantageously reduced variability of amplicon production in TMA reactions that included magnetic beads derivatized with oligo(dT). This decreased variability alternatively can be expressed as an increase in the "precision" of amplification. More particularly, the results presented below demonstrated that different reactions performed using substantially identical amounts of starting template polynucleotides advantageously gave more reproducible results where variability from sample to sample was reduced.

Although many different methods of detecting amplified polynucleotides can be used in connection with the present invention, the "Hybridization Protection Assay" (HPA) disclosed in U.S. Pat. No. 5,639,604, the disclosure of which is incorporated herein by reference, represents a particularly useful method. In one embodiment, the HPA detection method involves hybridizing amplified polynucleotides with a complementary polynucleotide probe that is labeled with a chemiluminescent acridinium ester. When hybridized in a duplex structure, the acridinium ester is protected from degradation under mild hydrolysis conditions. Acridinium ester in unhybridized probe molecules is susceptible to such degradation and is selectively destroyed by appropriate chemical treatment. Determining the amount of undegraded acridinium ester indicates the amount of probe that was hybridized to complementary polynucleotides. This determining step involves adding hydrogen peroxide to the mixture and measuring the amount of light emitted during a subsequent base-catalyzed chemiluminescence reaction. The HPA method of quantitating amplicon synthesis is preferred because there is no requirement for tedious and time consuming steps to remove excess unhybridized probe which otherwise would result in high levels of background hybridization. However, other methods for detecting and quantifying amplicons, such as procedures that employ radioactive, flourescent or enzyme-labeled probes or other detection methods which use separation methods including but not limited to solid-phase support formats, HPLC and electrophoresis, can be used in the practice of the invented method with equally good results. Indeed, the method used to detect amplicons is not expected to influence the quality of the results that would be obtained in the following procedures.

Preferred Analyte Polynucleotides

As described herein, quantitative methods employing pseudo targets can be used for conducting amplification reactions regardless of the origin of the analyte polynucleotide. Preferred analyte polynucleotides include nucleic acids from disease-causing organisms, including viruses, bacteria, fungi and protozoa. Examples of highly preferred analyte polynucleotides from viruses are nucleic acids from the human immunodeficiency viruses (HIV-1 and HIV-2), the hepatitis B virus (HBV), and the hepatitis C virus (HCV). Preferred analyte polynucleotides from bacteria, fungi and protozoa that can be quantitated according to the methods disclosed herein include the ribosomal RNAs (rRNA). Examples of bacteria that are highly preferred as sources of analyte polynucleotides include *Chlamydia trachomatis* (Gram-negative cells that are obligate intracellular organisms), members of the genus *Campylobacter* (*C. jejuni, C. coli, C. laridis*), members of the genus *Enterococcus* (*E. avium, C. casseliflavus, E. durans, E. faecalis, E. faecium, E. gallinarum, E. hirae, E. mundtii, E. pseudoavium, E. malodoratus, and E. raffinosus*), *Haemophilus influenzae, Listeria momocytogenes, Neisseria gonorrhoeae, Staphylococcus aureus, Group B Streptococci, Streptococcus pneumoniae, Mycobacterium tuberculosis, Mycobacterium avium, Mycobacterium intracellulare, Mycobacterium gordonae, Mycobacterium kansasii*. Examples of fungi that are highly preferred as sources of analyte polynucleotides include: *Blastomyces dermatitidis*, members of the genus *Candida* (*C. albicans, C. glabrata, C. parapsilosis, C. diversus, C. tropicalis, C. guilliermondii, C. dubliniensis*), *Histoplasma capsulatum, Coccidioides immitis*. Examples of protozoa that are highly preferred as sources of analyte polynucleotides include blood and tissue protozoa, such as members of the genus *Plasmodium* (*P. malariae, P. falciparum, P. vivax*), as well as protozoa which infect the gastrointestinal tract such as *Giardia lamblia* and *Cryptosporidium parvum*.

The invented method also can be used for quantifying nucleic acids that are of human origin, such as mRNAs that are over-expressed or under-expressed in disease states, including cancers. One example of gene that is present at an increased copy number in breast and ovarian adenocarcinomas is the HER-2/neu oncogene which encodes a tyrosine kinase having certain features in common with the epidermal growth factor receptor (EGFR). U.S. Pat. No. 4,968,603 describes the value of measuring the increased copy number of the HER-2/neu gene, or the HER-2/neu mRNA as a tool for determining neoplastic disease status. Thus, for example, the method described herein can be employed in quantitative nucleic acid amplification protocols whereby the cellular content of HER-2/neu polynucleotides is determined.

Indeed, the polynucleotide amplification method described herein is broadly applicable to numerous nucleic acid targets and is easily extended to procedures for quantifying any given analyte polynucleotide in a test sample.

Although other materials and methods similar or equivalent to those described herein can be used in the practice or testing of the present invention, the preferred methods and materials are now described. General references for methods that can be used to perform the various nucleic acid manipulations and procedures described herein can be found in *Molecular Cloning: A Laboratory Manual* (Sambrook, et al. eds. Cold Spring Harbor Lab Publ. 1989) and *Current Protocols in Molecular Biology* (Ausubel, et al. eds., Greene Publishing Associates and Wiley-Interscience 1987). Methods of performing the TMA reaction are disclosed in U.S. Pat. No. 5,399,491. Improvements to the TMA reaction protocol, such as that disclosed in U.S. Pat. No. 5,786,183, are embraced within the scope of Transcription Mediated Aamplification for the purpose of the present disclosure. Methods of preparing and using acridinium ester labeled probes are given by Arnold et al., in U.S. Pat. No. 5,639,604. The disclosures of these three patents are hereby incorporated by reference. A description of the experiments and results that led to the creation of the present invention now follows.

Example 1 describes methods which demonstrated that polynucleotide amplification reactions which included a pseudo target showed reduced variability of amplicon production.

EXAMPLE 1

Pseudo Target Amplification Reduces Variability in the Quantity of Amplicon Produced in TMA A series of TMA reactions was prepared using primers specific for a segment of the HIV pol transcript. All reactions were performed in replicates of eight. Each reaction received: 50 μl containing 60 copies of RNA transcripts of the complete HIV genome diluted in specimen buffer consisting of 10 mM HEPES (pH 7.5) and 1 mM EDTA. The RNA transcript had been synthesized using the plasmid BH10 as a template. In this procedure, the BH10 RNA was used as an exemplary analyte polynucleotide. The polynucleotide sequence of the BH10 RNA is given by the sequence of SEQ ID NO:3. Reactions also included either 0, $10^5$, $10^6$ or $10^7$ copies of the IAC-Ascr pseudo target RNA having the sequence of SEQ ID NO:4. There were added 25 μl of amplification reagent containing 10 pmols of a T7A (−)4190 primer having the sequence AATTTAATACGACTCACTATAGGGAGAGTTTGTATG-TCTGTTGCTAT- TATGTCTA (SEQ ID NO:1); 10 pmols of the (+)4108 primer having the sequence ACAGCAGTA-CAAATGGCAG (SEQ ID NO:2); 160 mM Tris buffer (pH 7.5); 16 mM each of ATP, CTP, GTP and UTP; 4 mM each of dATP, dCTP, dGTP and dTTP; 100 mM $MgCl_2$; 70 mM KCl; 20% glycerol; 0.6 mM zinc acetate and 20% polyvinylpyrrolidone. Samples were then overlaid with 200 μl of mineral oil, incubated first at 65° C. for 10 minutes to allow primer-target annealing, and then incubated at 42° C. for 5 minutes. Thereafter, each reaction received a 25 μl aliquot of enzyme mixture that contained 2,000 GP units of MMLV reverse transcriptase; 2,000 GP units of T7 RNA polymerase; 140 mM Tris buffer (pH 8.0); 100 mM N-acetyl-cysteine as a reducing agent; 20% glycerol; 70 mM KCl; 80 mM trehalose; 8 mM HEPES; 1.04 mM EDTA; 10% TRITON X-102 and 0.01% phenol red. One GP unit of reverse transcriptase corresponds to the amount of enzyme that synthesizes 5.75 fmols of cDNA from an RNA template in 15 minutes at 37° C. One GP unit of RNA polymerase is defined as the amount of enzyme that synthesizes 5 fmols of RNA transcript from a double stranded DNA template containing a promoter sequence in a period of 20 minutes at 37° C. Reactions were incubated at 42° C. for an additional 60 minutes. Thereafter, 100 μl samples of the reaction mixtures were combined with an equal volume of the HIV-specific AE(+)4134 probe bearing an acridinium ester moiety as the label and having the sequence CCACAATTTTAAAAGAAAAGGGGGGATTGG (SEQ ID NO:5). This labeled polynucleotide probe was prepared and used essentially according to the method disclosed in U.S. Pat. No. 5,639,604 and dispersed in a solution that included 100 mM lithium succinate buffer (pH 4.7), 2% (w/v) lithium lauryl sulfate, 1.2 M lithium chloride, 15 mM ardrithiol-2,20 mM EDTA, 20 mM EGTA and 3% ethanol. Substantially all of the ionic strength for promoting the hybridization reaction was provided by the 600 mM lithium chloride and 1% lithium lauryl sulfate components of the final hybridization solution. Importantly, the sequence of the AE(+)4134 probe permitted hybridization through complementary base pairing only with the analyte amplicon and not with the pseudo target amplicon. After hybridizing the mixture at 60° C. for 15 minutes, 300 μl of a selection reagent containing 600 mM sodium borate (pH 8.5) and 1% TRITON X-100 was added and the mixture incubated at 60° C. to inactivate unhybridized probe. Finally, the mixtures were cooled to room temperature, placed into a luminometer and the amount of analyte amplicon quantitated by measuring the light emitted from a chemiluminescent reaction (in RLUs). Detection reagent I included hydrogen peroxide solution in 0.001 N nitric acid. Detection reagent II included 1 N NaOH solution. Each reaction tube was injected first with detection reagent I, then with detection reagent II in order to stimulate light emission. Notably, probes used to detect and quantify the analyte amplicon were as follows: reactions not receiving the pseudo target were probed with 100 fmols of labeled AE(+)4134 probe (SEQ ID NO:5) and 3.9 pmols of unlabeled 2'methoxyribonucleotide (2'OMe) (+)4134; reactions that included $10^5$ copies of the pseudo target were probed using 100 fmols of labeled probe and 3.9 pmols of unlabeled 2'OMe (+)4134; reactions that included $10^6$ copies of the pseudo target were probed using 100 fmols of labeled probe and 0.2 pmols of unlabeled 2'OMe (+)4134; reactions that included $10^7$ copies of the pseudo target were probed using 100 fmols of labeled probe alone. Notably, 2'OMe has substituted a methoxy moiety for the hydroxyl moiety at the 2' position of the ribose in RNA. It should be noted that the (+)4134 polynucleotide had the same base sequence as the AE(+)4134 polynucleotide, but did not include the N-acridinium ester label. The different probe specific activities were employed to facilitate luminometry readings in a linear detection range.

The results presented in Table 1 indicated that amplification reactions which included a pseudo target advantageously gave more uniform results with less variability among the collection of samples. Table 1 shows the number of copies of IAC-Ascr pseudo target and BH10 RNA analyte polynucleotide included in each reaction. Also shown are the raw data representing the light emission from the reactions (in RLUs) and the net emission which has been corrected to subtract out the background emission measured in the negative control reactions. The column marked "Corrected to Uniform Sp. Act." indicates the value of the net RLUs that would be obtained if all HPA assays had been performed using the same high specific activity probe. This value was included in the analysis so that the different reactions could be compared directly. The net averages of all determinations for a given reaction condition are also presented along with the calculated values for standard deviation (SD) and coefficient of variability (CV%). The last column in the Table shows that the CV% values decreased as the number of copies of pseudo target in the reactions increased. This result quantitatively indicated that variability in the amount of amplicon produced in different reactions decreased as the amount of pseudo target was increased.

TABLE 1

Pseudo Target Amplification and Analyte Amplicon Synthesis Using Soluble Polynucleotides (Pure System)

| IAC-Ascr (copies) | BH10 RNA | RLUs | net RLUs | Corrected to Uniform Sp. Act. | net Avg. | Standard Deviation (SD) | Coefficient of Variability (CV %) |
|---|---|---|---|---|---|---|---|
| None | 60 | 60758 | 55366 | 2214640 | 2340305 | 1465936 | 62.6 |
| | | 100316 | 94924 | 3796960 | | | |
| | | 116898 | 111506 | 4460240 | | | |
| | | 80682 | 73500 | 3012000 | | | |
| | | 78084 | 72692 | 2907680 | | | |
| | | 31443 | 26051 | 1042040 | | | |
| | | 29419 | 24027 | 961080 | | | |
| | | 13587 | 8195 | 327800 | | | |
| | None | 5392 | 0 | 0 | 0 | | |
| 1.0 × $10^5$ | 60 | 85700 | 78257 | 3130280 | 3029790 | 1891104 | 62.4 |
| | | 64487 | 57044 | 2281760 | | | |
| | | 54852 | 47409 | 1896360 | | | |
| | | 41357 | 33914 | 1356560 | | | |
| | | 51353 | 43910 | 1756400 | | | |
| | | 93974 | 86531 | 3461240 | | | |
| | | 190926 | 183483 | 7339320 | | | |
| | | 82853 | 75410 | 3016400 | | | |
| | None | 7443 | 0 | 0 | 0 | | |
| 1.0 × $10^6$ | 60 | 580816 | 572789 | 1718367 | 1036444 | 323123 | 31.2 |
| | | 401651 | 393624 | 1180872 | | | |
| | | 302690 | 294663 | 883989 | | | |
| | | 222165 | 214138 | 642414 | | | |
| | | 275810 | 267783 | 803349 | | | |
| | | 322421 | 314394 | 943182 | | | |
| | | 349792 | 341765 | 1025295 | | | |
| | | 372722 | 364695 | 1094085 | | | |
| | None | 8027 | 0 | 0 | 0 | | |
| 1.0 × $10^7$ | 60 | 155174 | 146863 | 146863 | 134795 | 30825 | 22.9 |
| | | 138647 | 130336 | 130336 | | | |
| | | 102893 | 94582 | 94582 | | | |
| | | 157291 | 148980 | 148980 | | | |
| | | 166824 | 158513 | 158513 | | | |
| | | 149727 | 141416 | 141416 | | | |
| | | 181812 | 173501 | 173501 | | | |
| | | 92482 | 84171 | 84171 | | | |
| | None | 8311 | 0 | 0 | 0 | | |

Example 2 describes the methods used to demonstrate that enhanced precision of amplicon production was a general feature of reactions that included a pseudo target. More particularly, the following procedures showed that a second exemplary pseudo target, called IAC-Bscr, also reduced the variability of amplicon production in an exemplary TMA reaction.

EXAMPLE 2

Reduced Variability in the Production of Analyte Amplicons by TMA is a General Feature of Reactions that Included a Pseudo Target 30 μl containing 60 molecules of BH10 RNA diluted in specimen buffer (1 mM EDTA, 10 mM HEPES) was added to a series of reaction tubes. 20 μl containing 0, $10^5$, $10^6$, $10^7$ or $10^8$ IAC-Bscr pseudo target RNA molecules (SEQ ID NO:9) in specimen buffer was added to appropriate tubes. After vortexing, each tube received a 25 μl aliquot of amplification reagent described in Example 1, with the exception that the concentrations of the T7A(−)4190 and (+)4108 primers were used at 5 pmols each instead of 10 pmols. The liquid contents of each tube were then overlaid with 200 μl of oil to prevent evaporation. Tubes were incubated at 65° C. for 10 minutes and then at 42° C. for 5 minutes. A 25 μl aliquot of enzyme reagent as described in Example 1 was subsequently added to each tube. The contents of all tubes were mixed and the reactions incubated at 42° C. for 1 hour. At the end of the reaction period, all samples were subjected to analysis by standard HPA. Accordingly, 100 μl of a solution of acridinium labeled 2'methoxy AE(+)4134 probe was added to each tube. Different specific activities of the probe were used to detect analyte amplicons in samples produced using different amounts of the IAC-Bscr pseudo target. This ensured that light emission readings in the detection procedure would fall within the linear range of the luminometer that was used for quantifying analyte amplicons. Probes used to detect and quantify the analyte amplicon were as follows: reactions not receiving the pseudo target were probed with 100 fmols of labeled 2'OMe(+)4134 probe and 20.0 pmols of unlabeled probe; reactions that included $10^5$ copies of the pseudo target were probed using 100 fmols of labeled probe and 3.0 pmols of unlabeled probe; reactions that included $10^6$ copies of the pseudo target were probed using 100 fmols of labeled probe and 0.4 pmols of unlabeled probe; reactions that included $10^7$ or $10^8$ copies of the pseudo target were probed using 100 fmols of labeled probe alone. Mixtures of the amplification products and the probe were incubated at 60° C. for 15 minutes, mixed with 300 μl of selection reagent and then incubated at 60° C. for an additional 10 minutes. The mixtures were cooled to room temperature and chemiluminescence was read after adding detection reagents I and II.

The results presented in Table 2 confirmed that amplification reactions that included a pseudo target advantageously produced more uniform amounts of analyte amplicon with less variability among the collection of sample readings. Table 2 shows the number of copies of IAC-Bscr pseudo target and BH10 RNA analyte polynucleotide that were included in each of 8 replicate amplification reactions that were conducted for each level of input pseudo target. Also shown are the results representing the average net light emission readings from all HPA reactions. Background emission values measured for reactions that included the pseudo target without including the model analyte polynucleotide were subtracted to obtain the net results. The average amounts of analyte amplicon produced for each reaction condition ("Amplicon") are presented so that the products of different HPA reactions hybridized with probes having different specific activities could be compared directly. Also presented are values for standard deviation (SD) and coefficient of variability (CV%) that were calculated for all luminometry determinations for a given reaction condition. The results confirmed that the amounts of analyte amplicon synthesized in reactions that included a pseudo target were produced with greater precision than in reactions that did not include a pseudo target. More particularly, reactions that were conducted using greater than $1\times10^5$ pseudo target molecules yielded CV% values that were lower than the CV% value obtained for the data set produced from reactions conducted in the absence of a pseudo target. Indeed, the statistical "p" value was less than 0.05 for reactions in our data set that were performed using at least $10^6$ molecules of pseudo target. This quantitatively confirmed that variability in the amount of amplicon produced in different reactions decreased when the pseudo target was present.

TABLE 2

Pseudo Target Amplification and Analyte Amplicon Synthesis

| IAC-Bscr (copies) | BH10 RNA (copies) | Avg. net (RLU) | Amplicon (pmols) | Standard Deviation (SD) | Coefficient of Variability (CV %) |
|---|---|---|---|---|---|
| None | 60 | 165085 | 1.84 | 103009 | 62.4 |
| $1 \times 10^5$ | 60 | 193642 | 0.29 | 134671 | 69.5 |
| $1 \times 10^6$ | 60 | 164908 | 0.039 | 46096 | 28.0 |
| $1 \times 10^7$ | 60 | 96749 | 0.0029 | 30116 | 31.1 |
| $1 \times 10^8$ | 60 | 10199 | 0.0003 | 2475 | 24.3 |

Example 3 describes methods that were used to investigate whether amplification precision would also be enhanced for reactions performed in the presence of derivitized magnetic beads. In this procedure the beads were processed according to a standard specimen processing procedure which included a synthetic "target capture polynucleotide."

EXAMPLE 3

Precision of Amplicon Synthesis Improved for Reactions Performed in the Presence of Processed Magnetic Beads 100 μl of a target capture reagent was combined with an equal volume of HIV seronegative plasma. The target capture reagent included 17% lithium lauryl sulfate; 190 mM succinic acid; 250 mM lithium hydroxide; 3 mM EDTA; 3 mM EGTA; 3.5 nM deoxy (−)3737 capture probe having the sequence.

CCCTGTTTCTGCTGGAATAACTTCTGCTTCTATATT-TAAAAAAAAAAAAAAAAAAA AAAAAAAAAAA (SEQ ID NO:6) and 3.5 nM 2'methoxy (−)4258 A30 capture probe having the sequence.

TCTGCTGTCCCTGTAATAAACCCGTTTAAAAAAA-AAAAAAAAAAAAAAAAAAAAA AA (SEQ ID NO:7). The mixture was incubated at 60° C. for 20 minutes then combined with 20 μl of bead suspension including 120 μg of magnetic beads derivitized with oligo(dT) (Novagen; Madison Wis.). Reactions were then cooled to room temperature for 15 minutes to allow the hybridization of the capture probe and the immobilized oligo(dT). The beads were collected against the side of the vessel wall for 15 minutes upon positioning in a magnetic holder, and the supernatant aspirated. The beads were washed three times using 1 ml aliquots of wash reagent and used in a TMA reaction as described in Example 1, except that 100 copies of the BH10 RNA, and 0, $10^3$, $10^4$ or $10^5$ copies of the IAC Ascr pseudo target were used. HPA was carried out using 100 fmols of labeled AE(+)4134 probe and 200 fmols of unlabeled (+)4134 according to the procedure described above.

The results presented in Table 3 confirmed that amplification reactions that included a pseudo target advantageously yielded more uniform production of the analyte amplicon. More particularly, these results, which are based on replicates of 8 amplification reactions conducted for each level of input pseudo target, again indicated that the CV% values decreased for trials that had been performed in the presence of increasing amounts of pseudo target. Notably, levels greater than $10^4$ copies of pseudo target per reaction gave the most statistically significant improvement in the precision of analyte amplicon synthesis.

TABLE 3

| Pseudo Target Amplification and Analyte Amplicon Synthesis in the Presence of Derivitized Magnetic Beads | | | | |
|---|---|---|---|---|
| IAC-Ascr (copies) | BH10 RNA (copies) | net Avg. (RLU) | Standard Deviation (SD) | Coefficient of Variability (CV %) |
| None | 100 | 97105 | 37798 | 39.0 |
| $1.0 \times 10^3$ | 100 | 152313 | 38630 | 25.4 |
| $1.0 \times 10^4$ | 100 | 155062 | 67377 | 43.5 |
| $1.0 \times 10^5$ | 100 | 12385 | 19655 | 15.9 |

The results presented in the following Example confirmed that TMA reactions that included a pseudo target, and that employed analyte polynucleotides captured on an immobilized support, exhibited enhanced precision with respect to the amount of analyte amplicon synthesized in the amplification reaction. Whereas the procedures described under Example 3 proved that the presence of a solid phase capture substrate did not adversely affect the TMA reaction, the procedures set forth below more closely parallel the manner in which diagnostic testing procedures are carried out in accordance with the invention. More particularly, the procedures used in the following Example employed captured HIV RNA as amplification templates. Variability arising from inconsistent target recovery in these procedures was normalized to permit precision of amplification to be examined independently. More specifically, the HIV RNA was first collected on magnetic beads according to a standard specimen processing protocol and then pooled and redistributed into individual tubes so that all amplification reactions could be initiated with equal amounts of HIV RNA, but with different amounts of pseudo target.

Example 4 describes the methods used to demonstrate that TMA reactions conducted using pseudo targets and analyte polynucleotide templates captured on solid substrates gave enhanced precision of amplicon production in amplification reactions.

EXAMPLE 4

Pseudo Targets Enhance the Precision of Amplification Reactions that Employ Captured Analyte Polynucleotides as Templates 100 μl aliquots of target capture reagent and HIV virion suspension diluted in seronegative plasma containing either 0 or 200 copy equivalents of the HIV RNA/100 μl of plasma were combined in individual reaction tubes. Target capture reagent included the following reagents at the specified concentrations: 3 mM disodium EDTA; 3 mM EGTA; 17% lithium lauryl sulfate; 190 mM succinic acid (adjusted to a final pH 5.1); 250 mM lithium hydroxide; 3.5 nM deoxy HIV(−)3837 A30 (SEQ ID NO:6); and 3.5 nM 2'methoxy HIV(−)4258 A30 (SEQ ID NO:7). Samples were incubated at 60° C. for 20 minutes to liberate the HIV RNA from virions, to denature all polynucleotides and to allow the hybridization of capture probes to the target pol sequence. 20 μl aliquots of oligo(dT) bead suspension containing 120 μg of oligo(dT) derivatized beads were then added to each reaction tube. After mixing thoroughly, the samples were cooled to room temperature for 15 minutes to permit hybridization of the oligo(dA) tail of the capture probe and the bead-immobilized oligo(dT), thereby linking the analyte polynucleotide to the magnetic bead through a bridging polynucleotide. Beads and the polynucleotides immobilized thereon were isolated from plasma and free polynucleotides by placing the tubes on a magnetic rack for a period of 5 minutes, during which time the beads were collected against an inner surface of each tube. Supernatants were aspirated and the isolated beads washed three times using 1 ml aliquots of wash reagent (0.1% SDS, 10 mM HEPES (pH 7.5), 150 mM NaCl) with magnetic isolation of the beads between each step. The beads were next combined with 40 μl of specimen buffer (1 mM EDTA, 10 mM HEPES), mixed and pooled. 40 μl aliquots of the pooled bead suspension were then distributed to fresh reaction tubes so that all samples contained substantially identical amounts of bead-captured analyte polynucleotides. 10 μl aliquots of pseudo target diluted in specimen buffer (1 mM EDTA, 10 mM HEPES) were distributed to appropriate tubes. Each aliquot contained either 0, $2\times10^6$, $2\times10^7$ or $2\times10^8$ molecules of the IAC-Ascr or IAC Bscr pseudo target RNA. TMA amplification reactions were performed as described above in Example 2. Analyte amplicons were detected using a modified version of the HPA procedure called, "Adduct Promoted Hydrolysis" (APH). Following the amplification reactions, each tube received a 100 μl aliquot of acridinium labeled 2'OMe (+)4134 probe. Probes having different specific activities were used in this procedure so that amplification reactions performed using different amounts of pseudo target, whether IAC-Ascr or IAC-Bscr, would give light emission readings that fell in a linear response range for luminometry. These different specific activities were achieved by mixing labeled and unlabeled probes. Probes used to detect and quantify the analyte amplicon were as follows: reactions not receiving the pseudo target were probed with 1.0 pmol of labeled 2'OMe (+)4134 probe and 100.0 pmols of unlabeled probe; reactions that included $10^6$, $10^7$ or $10^8$ copies of the pseudo target were probed using 1.0 pmol of labeled probe and 1.0 pmol of unlabeled probe. Reactions were incubated at 60° C. for 15 minutes, mixed with 300 μl of sodium metaarsenite-containing selection reagent, and incubated at 60° C. for 20 minutes. The mixtures were cooled to room temperature and chemiluminescence was read after adding detection reagents I and II.

The results in Tables 4 and 5 confirmed that amplification reactions that included a pseudo target advantageously produced analyte amplicons in more uniform amounts and with less variability among the collection of sample readings. The Tables show that each reaction was primed using either 0 or 200 RNA equivalents of the HIV virion (strain HIV IIIb) as an analyte polynucleotide, and one of seven pseudo target conditions. The first condition was a negative control where the reactions were conducted in the absence of the pseudo target. The remaining conditions used either the IAC-Ascr (Table 4) or the IAC-Bscr (Table 5) pseudo target in one of three amounts. The summarized data in both Tables represents the results of 8 replicate trials conducted for each level of input pseudo target. Background emission values produced in reactions that included the pseudo target without including the model analyte polynucleotide template were subtracted to obtain the net results. The results clearly indicated that the amount of amplicon produced in the reactions decreased as the number of pseudo target molecules in the reaction increased, as expected. All amplification reactions that included a pseudo target resulted in the production of more uniform amounts of analyte amplicon. More particularly, the CV% values were lower among all data sets derived from reactions that included pseudo targets when compared to the negative control that was conducted in the absence of a pseudo target. These results supported the conclusion that precision in the amount of analyte amplicon produced in an amplification reaction can be improved by including a pseudo target in the reaction. The fact that two different pseudo targets gave similarly good results showed that the improved precision did not depend of the particular sequence of the pseudo target. These results further showed how precision in the amount of analyte amplicon produced in an amplification reaction can be improved by including pseudo targets in reactions that employed analyte polynucleotides captured by a solid support, such as a magnetic bead, as templates for the amplification reaction.

TABLE 4

Different Pseudo Targets Improve the Precision of Analyte Amplicon Production

| IAC-Ascr Pseudo Target (copies) | HIV Virion (copies) | Avg. net (RLU) | Amplicon (pmol) | Standard Deviation (SD) | Coefficient of Variability (CV %) |
|---|---|---|---|---|---|
| None | 200 | 69858 | 0.95 | 57195 | 81.9 |
| $2 \times 10^6$ | 200 | 166824 | 0.03 | 62799 | 37.6 |
| $2 \times 10^7$ | 200 | 26733 | 0.0041 | 13616 | 50.9 |
| $2 \times 10^8$ | 200 | 3043 | 0.0005 | 585 | 19.2 |

TABLE 5

Improved Precision of Analyte Amplicon Production Using Different Pseudo Targets

| IAC-Bscr Pseudo Target (copies) | HIV Virion (copies) | Avg. net (RLU) | Amplicon (pmol) | Standard Deviation (SD) | Coefficient of Variability (CV %) |
|---|---|---|---|---|---|
| None | 200 | 69858 | 0.95 | 57195 | 81.9 |
| $2 \times 10^6$ | 200 | 109125 | 0.0166 | 37519 | 34.4 |
| $2 \times 10^7$ | 200 | 14904 | 0.0023 | 10669 | 71.6 |
| $2 \times 10^8$ | 200 | 1492 | 0.0002 | 697 | 46.8 |

Figure 5:
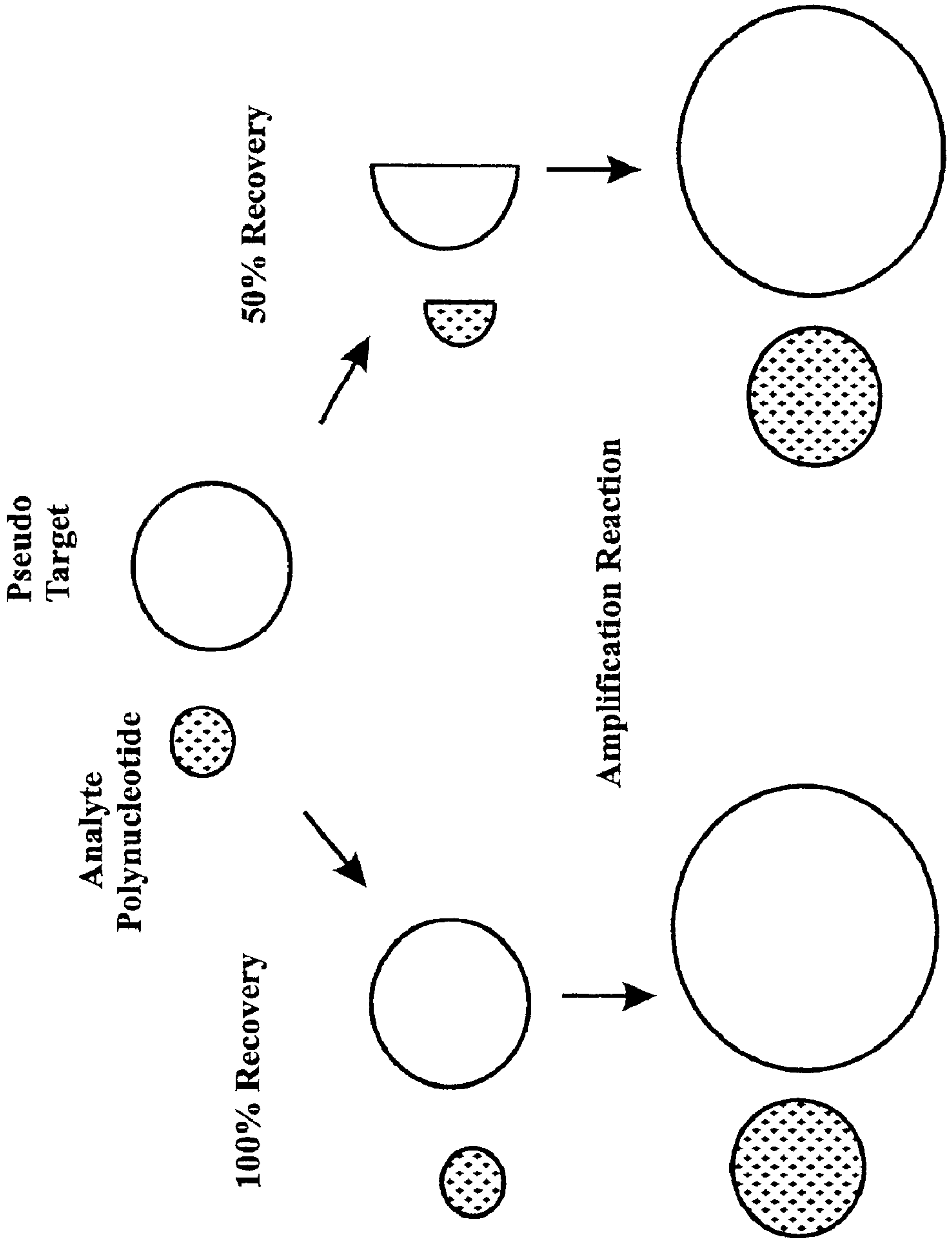

Yet another advantage of conducting amplification reactions in the presence of a pseudo target relates to normalizing the amount of amplicon produced when the input analyte polynucleotide is recovered from a biological sample at less than quantitative yield. The basis of this advantage, which is illustrated in FIG. 5, has been addressed above. The following Example was used to model situations wherein the recovery of analyte polynucleotides from a biological sample differed substantially. More particularly, conditions examined ranged from the equivalent of from 100% to 25% recovery. Such differences in the efficiency of analyte polynucleotide recovery could arise for reasons including variable recovery from phenol extraction procedures, ethanol precipitation procedures, difficult specimen collection or extraction conditions or even a laboratory spill leading to sample loss. In each case, the amount of analyte polynucleotide recovered would be less than a quantitative recovery.

As described below, the variable efficiency of analyte polynucleotide recovery was modeled by performing amplification reactions under three different conditions. Under the first condition, reactions were performed using three different amounts of input analyte polynucleotide without pseudo target. The second condition involved reactions performed using the same three different amounts of input analyte polynucleotide and a constant amount of pseudo target. Finally, the third reaction condition employed the same three different amounts of input analyte polynucleotide, where the ratio of the amounts of analyte polynucleotide and pseudo target were constant. It will be apparent that this third condition represents a case which would result when the pseudo target was added to a biological sample containing analyte polynucleotide at a time before nucleic acids were isolated from the sample. Under this circumstance, loss of a portion of the sample during processing steps would result in identical percentage losses of both analyte polynucleotide and pseudo target, yet the ratio of the two species would remain fixed. As will be apparent from the results that follow, amplification reactions that included a constant ratio of pseudo target and analyte polynucleotide advantageously gave improved synthesis of analyte amplicons. Thus, even reactions having a limited number of input analyte polynucleotides behaved as though the starting number of templates was larger.

The results obtained in the Example which follows provided the basis for the improved method of biological specimen processing that includes adding pseudo targets to the specimen before nucleic acids are isolated. One method of normalizing the level of analyte amplicon produced in an amplification reaction involves first adding the pseudo target to a biological specimen, then isolating polynucleotides from the specimen and thereafter using the polynucleotides isolated in this fashion to conduct the amplification reactions.

Example 5 describes the methods that were used to represent amplification reactions that were initiated using variable amounts of analyte polynucleotide. More particularly, the reactions were performed so that the amounts of analyte polynucleotide represented "100%," "50%" and "25%" values.

EXAMPLE 5

Normalizing Amplicon Synthesis in Amplification Reactions Primed with Variable Amounts of Analyte Polynucleotide Amplification reactions were prepared according to the method of Example 1 with the following changes. First, replicates of 10 reactions for each condition were prepared instead of replicates of eight. Second, primer amounts used in the reactions were reduced to 5 pmols each, instead of 10 pmols each. Third, 20% polyvinylpyrrolidone was substituted by 10% trehalose. Fourth, the amounts of analyte polynucleotide and pseudo target were as presented in Table 6. In our procedures, the polynucleotide mixtures presented in this Table were first combined, then mixed with other reagents in the reaction mixture, and finally mixed with the two polymerase enzymes to initiate the TMA reaction.

TABLE 6

Mixtures of Analyte Polynucleotide and Pseudo Target

| Condition | BH10 RNA (copies) | IAC-Ascr (copies) |
|---|---|---|
| No | 500 | 0 |
| Pseudo Target | 1000 | 0 |
| | 2000 | 0 |
| Constant | 500 | $6 \times 10^6$ |
| Pseudo Target | 1000 | $6 \times 10^6$ |
| | 2000 | $6 \times 10^6$ |
| Constant Ratio of Pseudo | 500 | $1.5 \times 10^6$ |
| Target and Analyte | 1000 | $3.0 \times 10^6$ |
| Polynucleotide | 2000 | $6.0 \times 10^6$ |

At the conclusion of the amplification reactions, all reaction mixtures were probed according to the APH protocol described above in Example 4 to detect and quantitate analyte amplicons. AE labeled HIV (+)4134b probe having the sequence CCACAATTTTAAAAGAAAAGGG (SEQ ID NO:8) of different specific activities was used in this procedure so that the amplification reactions performed using different amounts of pseudo target would give light emission readings that fell within a linear response range for luminometry. Again, these different specific activities were achieved by mixing different amounts of labeled and unlabeled probes. Probes used to detect and quantify the analyte amplicon were as follows: reactions not receiving the pseudo target were probed using 1.3 pmols of labeled probe and 400 pmols of unlabeled probe; reactions that included $1.5\times10^6$, $3\times10^6$ or $6\times10^6$ copies of pseudo target were probed using 1.3 pmols of labeled and 8.7 pmols of unlabeled probe.

Figure 6:
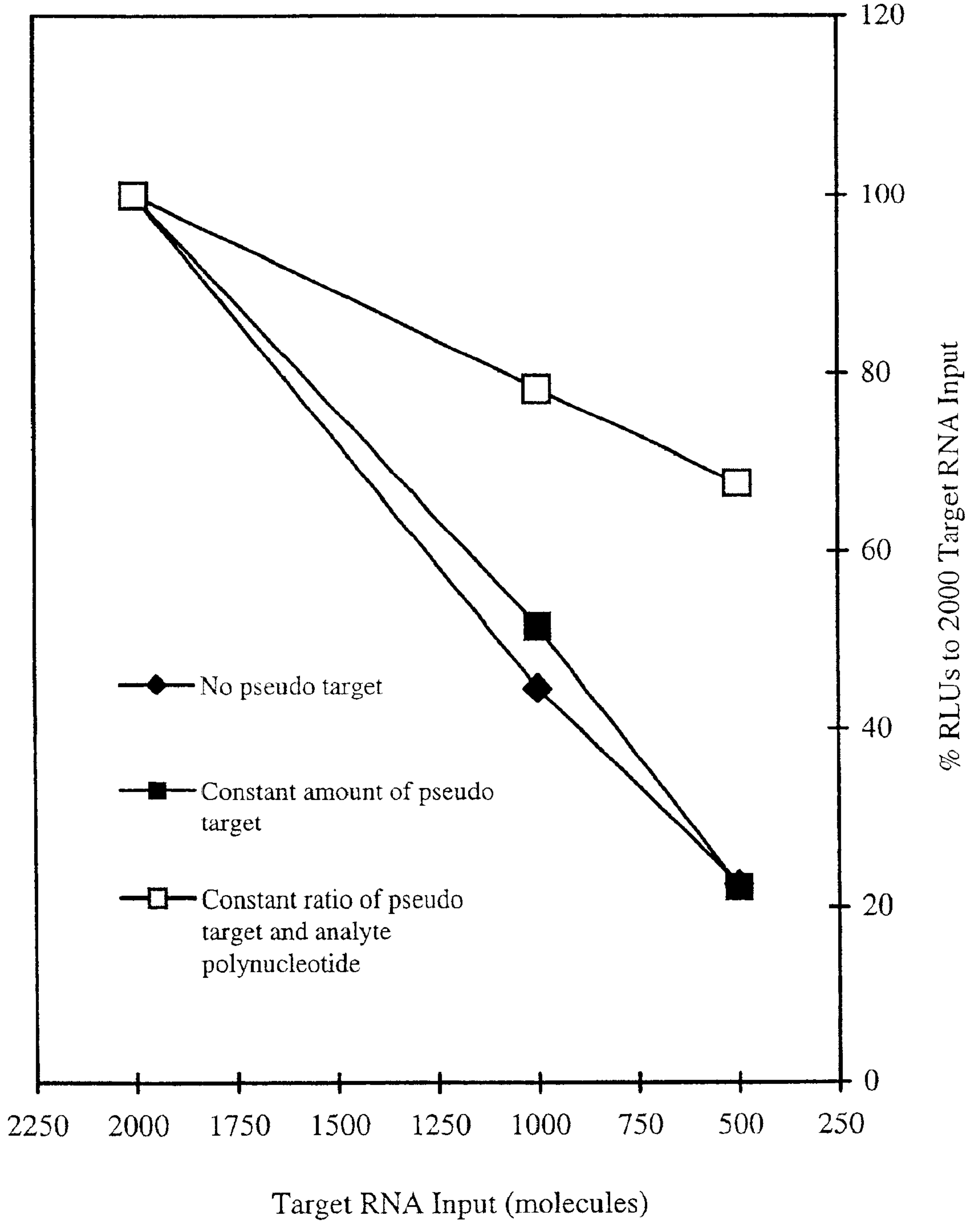
FIG. 6 is a line graph showing how a pseudo target can be used to normalize amplicon synthesis in amplification reactions given different amounts of analyte polynucleotide. The three conditions presented in the graph are: no pseudo target (♦); constant amount of pseudo target (■); and constant ratio of pseudo target and analyte polynucleotide (□).

The quantitative results presented in Tables 7–9 and in FIG. 6 clearly indicated that reactions in which the ratio of pseudo target to analyte polynucleotide was held constant yielded substantially smaller differences in the amounts of analyte amplicon synthesized from variable amounts of input analyte polynucleotide. All results were based on replicates of 10 trials conducted for each level of input analyte polynucleotide template. In FIG. 6, 100% of input analyte polynucleotide was represented by 2,000 copies of BH10 RNA. In the absence of pseudo target the slope of the line representing the amount of analyte amplicon produced at decreasing levels of input analyte polynucleotide, declined sharply as the number of these template decreased from 2,000 to 500. A similar result was obtained in the trials containing a constant level of pseudo target. Thus, procedures that involved merely adding pseudo target to a sample having a low level of input analyte polynucleotides had substantially no effect on increasing the amount of analyte amplicon that was synthesized. However, the amplification reactions that were carried out using a constant molar ratio of pseudo target to analyte polynucleotide yielded smaller differences in the amounts of analyte amplicon synthesized from variable amounts of input analyte polynucleotide. For example, the results shown in the Figure indicate that at 500 copies of input BH10 RNA, the yield of analyte amplicons (measured in RLU) was about 68% of the value obtained using 2000 copies of the template, while the corresponding result obtained in the absence of pseudo target or when pseudo target was held constant only was about 22%. Conducting amplification reactions using a constant ratio of pseudo target and analyte polynucleotide tended to normalize the amount of analyte amplicon synthesized in the amplification reaction. Also, the ratio may be varied somewhat depending on input level and desired accuracy of quantitation. Significantly, substantially similar results were obtained when the reactions were conducted in the presence of magnetic beads and a capture reagent, as described under Examples 3 and 4. Moreover, the data presented in Tables 7–9 show that precision of amplification reactions was improved by including a pseudo target in the amplification reaction.

TABLE 7

TMA Reactions Conducted in the Absence of a Pseudo Target

| BH10 RNA (copies) | net Avg (RLU) | % of 2000 | Standard Deviation (SD) | Coefficient of Variability (CV %) |
|---|---|---|---|---|
| None | 0 | 0 | N/A | N/A |
| 500 | 35279 | 22.4 | 10033 | 28.4 |
| 1000 | 70202 | 44.7 | 36070 | 51.4 |
| 2000 | 157176 | 100 | 26792 | 17.0 |

TABLE 8

TMA Reactions Having Constant Pseudo Target Levels

| BH10 RNA (copies) | net Avg (RLU) | % of 2000 | Standard Deviation (SD) | Coefficient of Variability (CV %) |
|---|---|---|---|---|
| None | 0 | 0 | N/A | N/A |
| 500 | 96434 | 22.2 | 23442 | 24.3 |
| 1000 | 224493 | 51.6 | 49903 | 22.2 |
| 2000 | 434899 | 100 | 30382 | 7.0 |

TABLE 9

TMA Reactions Having a Constant Ratio of Analyte Polynucleotide and Pseudo Target

| BH10 RNA (copies) | net Avg (RLU) | % of 2000 | Standard Deviation (SD) | Coefficient of Variability (CV %) |
|---|---|---|---|---|
| None | 0 | 0 | N/A | N/A |
| 500 | 294660 | 67.8 | 43197 | 14.7 |
| 1000 | 340594 | 78.3 | 72128 | 21.2 |
| 2000 | 434899 | 100 | 30382 | 7.0 |

The following Example describes experiments that were carried out to show how incorporating a pseudo target into an amplification reaction can be used to control the amount of amplicon produced in the reaction. As indicated above, reducing the amount of amplicon produced in a reaction advantageously: (1) reduces the likelihood of positive carry-over contamination; (2) allows for more efficient use of labeled probes; and (3) may be used to "tune" signal strength to fall within a linear range for detection apparatus such as a luminometer. With respect to this second point, with reduced numbers of product amplicon produced in a reaction it becomes possible to employ very high specific activity probes in quantities sufficient to provide probe excess. Those having an ordinary level of skill in the art will appreciate that the specific activity of a hybridization probe refers to the amount of detectable label per probe molecule. High specific activity probes are useful for detecting minute quantities of complementary polynucleotides. However, if the probe is expensive to prepare, or is labeled with a radioactive label that requires special handling and disposal precautions, it may not be desirable to use high specific activity probes in large quantities that would be needed to carry out quantitative hybridizations using probe excess conditions. Thus, reducing the amount of analyte amplicon produced in an amplification reaction advantageously can facilitate efficient use of probes that are employed for detecting the amplicons.

Example 6 describes methods that were used to demonstrate how pseudo targets can be used to control the amount of analyte amplicon produced in an amplification reaction.

EXAMPLE 6

Employing Pseudo Targets to Control the Production of Analyte Amplicons

100 $\mu$l of target capture reagent (17% lithium lauryl sulfate; 190 mM succinic acid; 250 mM lithium hydroxide; 3 mM EDTA; 3 mM EGTA; 3.5 nM 2'methoxy (−)3837 A30 capture probe (SEQ ID NO:6) and 3.5 nM 2'methoxy (−)4258 A30 capture probe (SEQ ID NO:7) was combined with 100 $\mu$l of HIV virion diluted in HIV seronegative plasma. Samples contained either no HIV RNA; 200; 2,000; 20,000; 200,000 or 2,000,000 RNA equivalents/ml of plasma. Mixtures were incubated at 60° C. for 20 minutes to allow hybridization of the capture probe with pol gene sequences present in target polynucleotides, and then combined with 20 μl of oligo(dT) bead suspension (120 μg of oligo(dT) beads/20 μl). After mixing thoroughly, samples were cooled to room temperature over a period of 15 minutes to allow hybridization of the oligo(dA) of the capture probe and the bead-immobilized oligo(dT), thereby linking the pol gene sequence and the magnetic bead. Beads were collected against the sides of the tubes using a magnetic rack and the supernatants aspirated. Beads were washed three times using 1 ml volumes of wash reagent (0.1% SDS; 10 mM HEPES (pH 7.5); 150 mM NaCl). 50 μl aliquots of specimen buffer (10 mM HEPES; 1 mM EDTA) were added to tubes that did not receive any pseudo target. 50 μl aliquots of pseudo target diluted in specimen buffer were added to tubes that did receive the pseudo target. After mixing, each sample received a 25 μl aliquot of amplification reagent containing: 5 pmols of a T7A(−)4190 primer; 5 pmols of the (+)4108 primer; 160 mM Tris buffer (pH 7.5); 16 mM each of ATP, CTP, GTP and UTP; 4 mM each of dATP, dCTP, dGTP and dTTP; 100 mM $MgCl_2$; 70 mM KCl; 20% glycerol; 0.6 mM zinc acetate and 10% trehalose. Samples were overlaid with 200 μl of mineral oil and then incubated at 42° C. for 10 minutes. Amplification reactions were initiated by adding 25 μl aliquots of enzyme reagent containing 2000 GP units of MMLV reverse transcriptase; 2000 GP units of T7 RNA polymerase; 140 mM Tris buffer (pH 8.0); 100 mM N-acetyl-cysteine as a reducing agent; 20% glycerol; 70 mM KCl; 80 mM trehalose; 8 mM HEPES; 1.04 mM EDTA; 10% TRITON X-102 and 0.01% phenol red. All reactants were mixed and allowed to incubate at 42° C. for 1 hour.

At the conclusion of the reaction period, analyte amplicons were quantified using the above-described APH procedure. A 100 μl aliquot of a solution of acridinium labeled probe AE(+)4134b was added to each sample. Samples corresponding to reactions that included the pseudo target received 1.3 pmols of labeled probe and 38.7 pmols of unlabeled probe, while samples corresponding to reactions that did not include the pseudo target received 1.3 pmols of labeled probe and 400 pmols of unlabeled probe. Mixtures were incubated at 60° C. for 15 minutes and then combined and mixed with 300 μl of APH selection reagent containing sodium metaarsenite. Reaction mixtures were incubated at 60° C. for 20 minutes and then cooled to room temperature. Chemiluminescence was read following addition of detection reagents I and II.

Notably, preliminary experiments were carried out in which routine APH procedures were conducted using a range of specific activities to identify conditions that would give results falling within the linear detection range of the luminometer used in our experiments. Those having ordinary skill in the art readily will appreciate that many sorts of detection apparatus, whether a luminometer or an X-ray film, have a range within which the intensity of a signal and the amount of material that produced the signal are linearly or exponentially related. Above that range, the correspondence does not hold. Thus, determining such linear ranges is a matter of routine experimentation for those having ordinary skill in the art.

The probe mixtures employed for detecting analyte amplicons in our procedure were: 401.3 pmols of probe consisting of 1.3 pmols labeled probe and 400 pmols of unlabeled probe for the reaction conducted in the absence of a pseudo target; and 40 pmols of probe consisting of 1.3 pmols labeled probe and 38.7 pmols of unlabeled probe for the reaction that included the pseudo target. In order to normalize the results of the assay, light intensity readings (measured in RLUs) were converted into pmols of amplicon in the hybridization step by multiplying the average net RLU values by a conversion factor. This conversion factor was established by hybridizing, in parallel reactions, known amounts of target polynucleotide and excess amounts of labeled probe and then determining the light output generated by the known amount of target. This allowed correlation of light output and the amount of amplicon hybridized to the probe.

Figure 7:
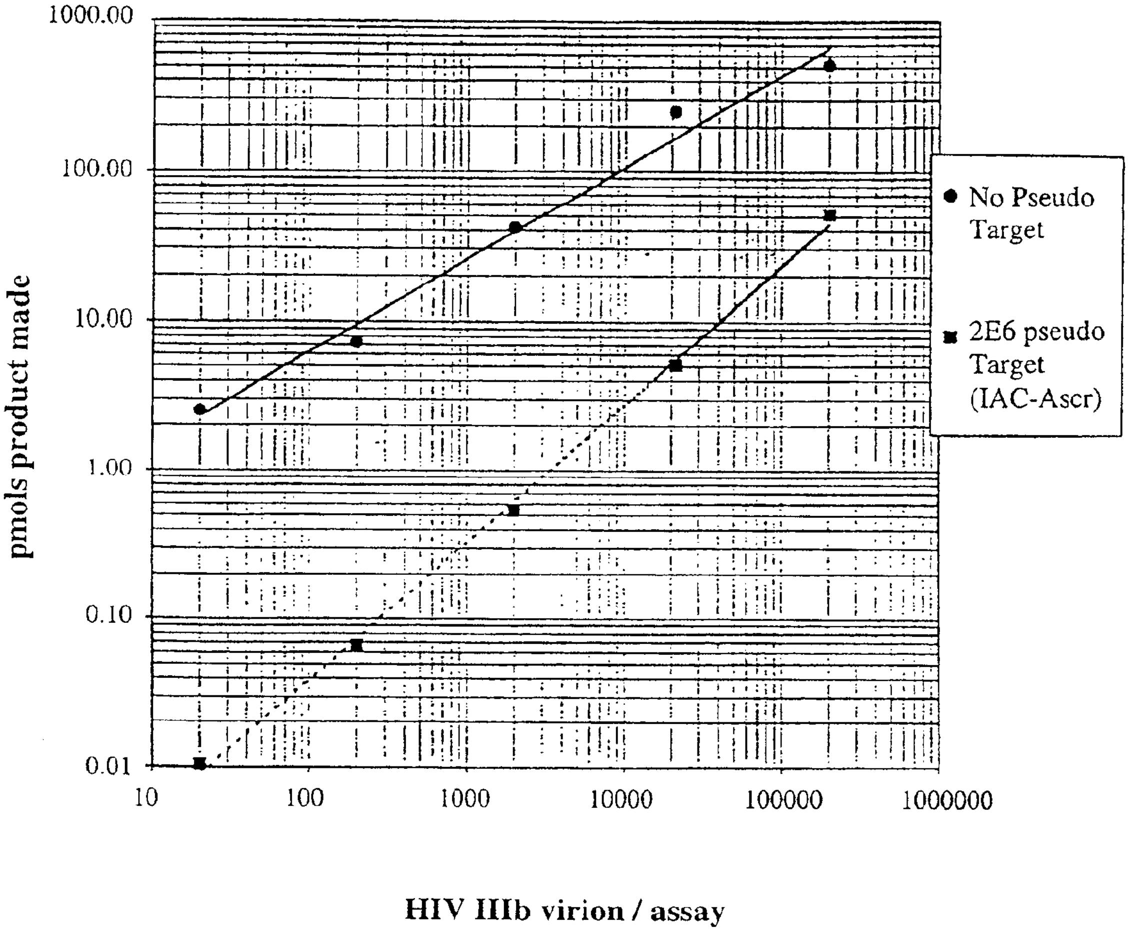
FIG. 7 is a line graph showing how a pseudo target can be used to control the production of analyte amplicons. The two conditions presented in the graph are: no pseudo target (●); and $2\times10^6$ copies of pseudo target per reaction (■).

The results presented in Tables 10 and 11 and in FIG. 7 indicated that the presence of a pseudo target in an amplification reaction did not compromise the correlation between the amount of input analyte polynucleotide and the amount of analyte amplicon produced in amplification reactions. All results were based on replicates of 5 trials conducted for each level of input HIV IIIb RNA used in the procedure. The log plot shown in FIG. 7 clearly indicates a strong relationship between the amount of HIV IIIb RNA equivalents input into a reaction and the amount of analyte amplicon produced. Clearly, this same strong linear relationship prevailed when the amplification reactions additionally included the pseudo target. The downward shift observed for the line representing analyte amplicons produced in reactions that included pseudo targets indicates that fewer molecules were produced when compared with reactions that did not include pseudo targets. For example, the results shown in Table 10 indicate that approximately 520 pmols of analyte amplicon were produced in the reaction that included 200,000 HIV RNA equivalents, and that this number was reduced by about ten fold when the pseudo target was included in the reaction. Thus, the number of analyte amplicons produced in the amplification reaction was reduced by including a pseudo target in the reaction.

TABLE 10

Controlling Analyte Am licon Production Using Pseudo Targets

| HIV IIlb RNA equivalents/reaction | No Psuedo Target Avg net (RLU) | Amplicon (pmols) | Standard Deviation (SD) |
|---|---|---|---|
| None | 0 | 0 | N/A |
| 20 | 47878 | 2.5 | 55529 |
| 200 | 137756 | 7.2 | 143360 |
| 2000 | 794621 | 41.7 | 174616 |
| 20,000 | 4762815 | 250 | 609171 |
| 200,000 | 9908427 | 520 | 639895 |

TABLE 11

Controlling Analyte Amplicon Production Using Pseudo Targets

| HIV IIlb RNA equivalents/reaction | 2 × $10^6$ Pseudo Target Molecules (IAC-Ascr) Avg net (RLU) | Amplicon (pmols) | Standard Deviation (SD) |
|---|---|---|---|
| None | 0 | 0 | N/A |
| 20 | 1623 | 0.01 | 2224 |
| 200 | 10473 | 0.067 | 8000 |
| 2000 | 84435 | 0.54 | 8449 |
| 20,000 | 802975 | 5.1 | 189079 |
| 200,000 | 8083585 | 51.5 | 1567615 |

Qualitative Format Assays

Although the foregoing description relates to quantitative assays, other useful procedures that employ pseudo targets in amplification reactions relate to qualitative assays that provide information about the presence or absence of an analyte polynucleotide in a test sample. Qualitative tests can also be used for indicating whether or not an analyte polynucleotide in a test sample is present at a level falling within a specified range. These assays could, for instance, be used to monitor a patient's response to drug therapy. For example, a patient infected with a blood borne virus may experience a change in the plasma titer following therapeutic drug treatment. A physician can monitor whether the patient's virus titer increases or decreases with respect to a particular threshold value using a qualitative assay that incorporates pseudo target amplification. It is to be understood that a qualitative testing format involves only detection of a signal and so would not necessarily require quantitative measurement of the signal or the production or use of a standard curve by an end-user of a diagnostic assay.

In certain preferred embodiments of the invention qualitative assays are performed to indicate whether a biological sample contains an analyte polynucleotide. In other preferred embodiments of the invention assays that produce only qualitative results (i.e., a result is either positive or negative) but can provide semi-quantitative information about an analyte polynucleotide in a sample.

Qualitative assays that co-amplify analyte polynucleotides and pseudo targets are especially versatile when combined with detection protocols having specified thresholds of detection. These thresholds can be manipulated by adjusting the specific activity of a hybridization probe, or by calibrating the detection device to specify a negative result below a certain numerical value or a positive result above a certain value. For example, a luminometer can be set to indicate a positive result for RLU values greater than a certain threshold level. Alternatively, the amount of pseudo target included in the amplification reaction can be increased or decreased so that certain levels of analyte amplicon produce detectable signals that are either above or below the limit of detection for a particular device. Thus, the amount of pseudo target input into an amplification reaction for a diagnostic assay can be adjusted or "tuned" through routine experimentation so that a detection signal falling within a desired range is produced.

When an analyte polynucleotide and a pseudo target are co-amplified according to the above-described procedures, the amount of analyte amplicon synthesized in the reaction will naturally be related to the amount of analyte polynucleotide that was input into the reaction. Since the magnitude of a hybridization signal can be tuned by one of the procedures described above, since amplification reactions that incorporate pseudo targets advantageously are characterized by enhanced precision, and since it is possible to tune a diagnostic reaction so that a given level of input analyte polynucleotide produces a hybridization signal that is above or below a detection threshold for a testing instrument it is possible to produce qualitative assays that also provide quantitative information.

The following Example illustrates how semi-quantitative information about the amount of analyte polynucleotide in a test sample can be obtained using a qualitative assay that provides only positive or negative results. For illustrative purposes, the HIV polynucleotide serves as the analyte polynucleotide and the indicated titer range is based on results presented in the previous Example. Of course, other analyte polynucleotides and different threshold ranges also can be employed in this qualitative testing format. Also, detection by luminometry can be substituted by fluorescence or other optical or electro-chemical detection methods. Pseudo target can be combined with a biological sample and nucleic acids isolated thereafter, or simply combined with pre-isolated analyte polynucleotide prior to the co-amplification step. In this Example the detection system includes a detection device (luminometer), a labeled hybridization probe that can be detected by the detection device. Based on the preceding description it should be clear that the specific activity of the labeled probe and the amount of pseudo target included in the co-amplifying step are both variables that can be manipulated to contro the threshold of detection in the detection system.

Example 7 describes how amplification reactions that include pseudo targets can be used in a qualitative assay format to derive semi-quantitative information about pre-amplification amounts of analyte polynucleotide.

EXAMPLE 7

Qualitative Assay Formats

A physician treating a patient infected with HIV desires to monitor the effectiveness of a drug treatment protocol. The physician specifically desires to know when the patient's plasma titer is reduced from a high starting level to a lower level that corresponds to below about 200 RNA equivalents in 100 $\mu$l of plasma.

First and second plasma samples are obtained from the patient at times before and after commencing drug therapy. Samples are prepared and used for amplification reactions essentially as described under Example 6. Individual 100 $\mu$l aliquots of the plasma samples are mixed with 100 $\mu$l aliquots of target capture reagent and the mixtures incubated, combined with oligo(dT) bead suspension, mixed again and then cooled to room temperature. Beads are collected, washed and then combined with 50 $\mu$l aliquots containing $2\times10^6$ copies of pseudo target diluted in specimen buffer. After mixing, each sample receives a 25 $\mu$l aliquot of amplification reagent containing primers and nucleotide reactants. Samples are overlaid with 200 $\mu$l of mineral oil and then incubated at 42° C. for 10 minutes. Amplification reactions are initiated by adding 25 $\mu$l aliquots of enzyme reagent containing 2000 GP units of MMLV reverse transcriptase and 2000 GP units of T7 RNA polymerase in a buffered solution. All reactants are mixed and allowed to incubate at 42° C. for 1 hour. Amplified samples are then subjected to an APH detection procedure. A solution of acridinium labeled probe AE(+)4134b is added to each sample. Each sample receives 1.3 pmols of labeled probe and 38.7 pmols of unlabeled probe, where each probe is specific for authentic HIV amplicons but not pseudo target amplicons. These amounts of probe represent saturating hybridization amounts so that analyte amplicons will be quantitatively detected. Mixtures are incubated at 60° C. for 15 minutes and then combined and mixed with 300 $\mu$l of APH selection reagent containing sodium metaarsenite. Reaction mixtures are incubated at 60° C. for 20 minutes and then cooled to room temperature. Chemiluminescence is read following addition of detection reagents I and II using a luminometer programmed to indicate a positive result for RLU values of 10,000 or greater and a negative result for RLU values less than 10,000. The pre-treatment plasma sample gave a positive result, thereby indicating a level of at least about 200 RNA equivalents. Conversely, the post-treatment plasma sample gave a negative result, thereby indicating a level of less than 200 RNA equivalents in the 100 $\mu$l sample. The physician judges that the drug treatment is effective at reducing viral load.

This invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims.

What is claimed is:

1. A method of determining whether an analyte polynucleotide is present in a test sample in an amount greater or less than a pre-determined value, comprising the steps of:

obtaining a test sample to be analyzed for the presence of said analyte polynucleotide, said analyte polynucleotide being selected from the group consisting of a viral polynucleotide, a bacterial polynucleotide, a fungal polynucleotide, a protozoan polynucleotide, and a human polynucleotide;

combining said test sample with an amount of a pseudo target;

co-amplifying in a polynucleotide amplification reaction the pseudo target and any analyte polynucleotide contained in said test sample to produce amplification products that include a pseudo target amplicon and an analyte amplicon, wherein said analyte amplicon is produced in an amount that is dose-dependent on the amount of said analyte polynucleotide present in said test sample, and wherein said pseudo target and said analyte polynucleotide are co-amplified using the same set of two oligonucleotide primers; and quantitatively detecting said analyte amplicon using a detection system calibrated to indicate a positive result upon detecting an amount of analyte amplicon arising from co-amplification of said amount of said pseudo target and an amount of analyte polynucleotide equal to or greater than said pre-determined value, wherein the amount of said pseudo target in the combining step is greater than said pre-determined value and is sufficient to reduce production and to reduce a coefficient of variability of said analyte amplicon relative to analyte amplicon that would be produced in an identical polynucleotide amplification reaction that omitted said pseudo target, wherein said positive result indicates that said analyte polynucleotide is present in said test sample in an amount equal to or greater than said pre-determined value, wherein a negative result indicates that said analyte polynucleotide is present in said test sample in an amount less than said pre-determined value, and wherein said positive result and said negative result are determined without reference to the amount of pseudo target amplicon synthesized in the co-amplifying step.

2. The method of claim 1, further comprising a step for detecting the pseudo target amplicon produced in the co-amplifying step.

3. The method of claim 1, wherein said detection system comprises luminometry.

4. The method of claim 1, wherein said analyte polynucleotide is a viral polynucleotide.

5. The method of claim 4, wherein said viral polynucleotide is selected from the group consisting of an HIV-1 polynucleotide, an HIV-2 polynucleotide, an HBV polynucleotide, and an HCV polynucleotide.

6. The method of claim 1, wherein said detection system is selected from the group consisting of a chemiluminescent detection system, a fluorescent detection system, an optical detection system, and an electro-chemical detection system.

* * * * *